United States Patent [19]
Yamakoshi et al.

[11] Patent Number: 5,698,585
[45] Date of Patent: Dec. 16, 1997

[54] PHARMACEUTICAL PREPARATION FOR PREVENTION AND/OR TREATMENT FOR CATARACT

[75] Inventors: Jun Yamakoshi; Tsutomu Sasaki; Hiroharu Ishikawa; Yukihiko Iwai; Takanao Matsudo, all of Chiba; Kenji Mori, Tokyo; Mamoru Kikuchi, Chiba, all of Japan

[73] Assignee: Kikkoman Corporation, Chiba, Japan

[21] Appl. No.: 631,424

[22] Filed: Apr. 12, 1996

[30] Foreign Application Priority Data

Apr. 13, 1995 [JP] Japan .................................. 7-111017
Oct. 12, 1995 [JP] Japan .................................. 7-264526
Oct. 12, 1995 [JP] Japan .................................. 7-264527

[51] Int. Cl.⁶ .................................................. A61K 31/34
[52] U.S. Cl. .................... 514/472; 514/461; 514/912
[58] Field of Search .................................. 514/472, 461, 514/912

[56] References Cited

PUBLICATIONS

WPIDS085438, 1986. Imanaka et al.

*Primary Examiner*—Zohreh Fay
*Attorney, Agent, or Firm*—Fish & Richardson, P.C.

[57] ABSTRACT

In order to prevent or treat cataract, present invention features 3(2H)-furanone derivatives having 3(2H)-furanone skeleton as a main structure and/or pharmaceutically acceptable salts thereof, pharmaceutical preparations containing the derivatives and/or the salts thereof, treatment methods of cataract, and their use. The 3(2H)-furanone derivatives have excellent effects for the prevention and/or treatment of cataract, for instance, senile cataract caused by oxidation disorder. Particularly, the pharmaceutical preparations have good effect for the prevention and/or treatment of cataract when they are administrated as ophtalmics.

9 Claims, 6 Drawing Sheets

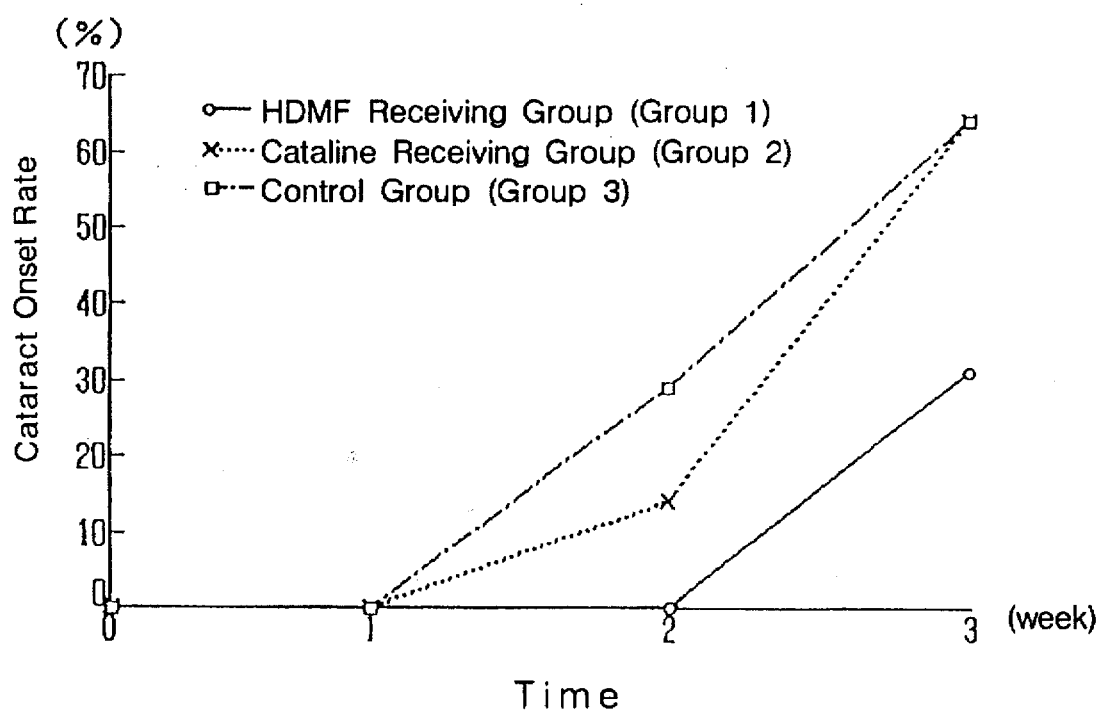

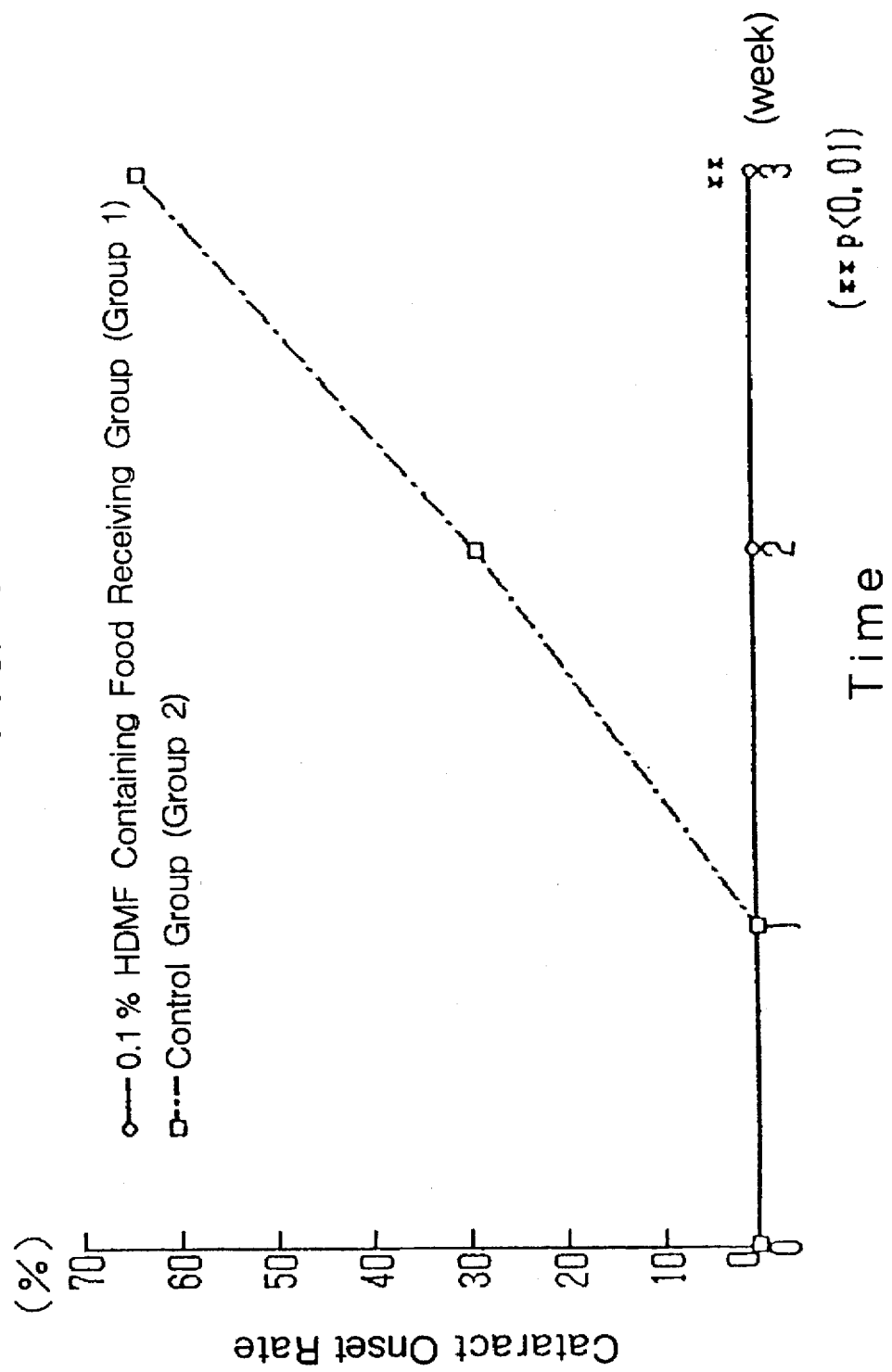

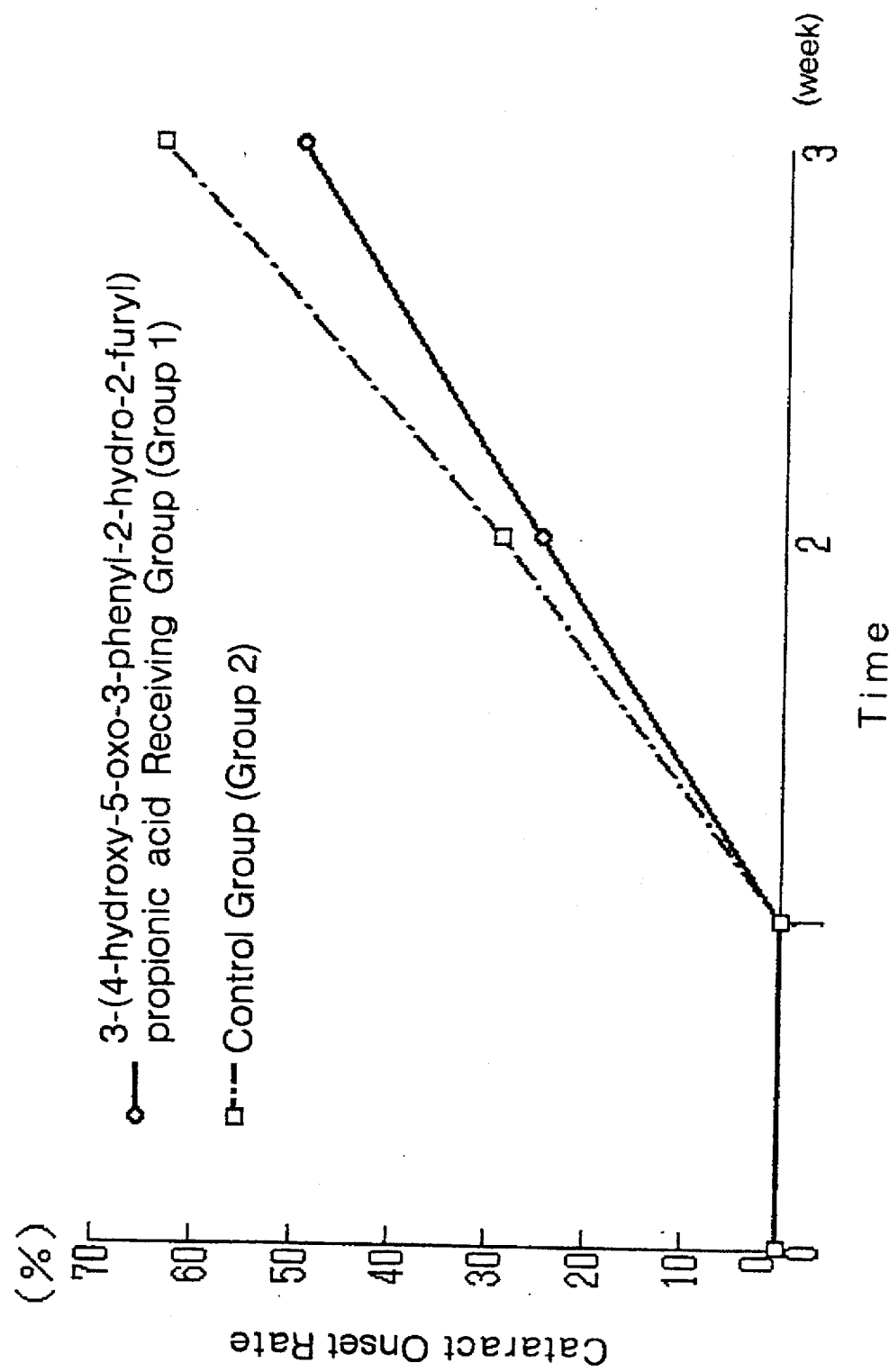

PHARMACEUTICAL PREPARATION FOR PREVENTION AND/OR TREATMENT FOR CATARACT

TECHNICAL FIELD

The present invention relates to a pharmaceutical preparation for prevention and/or treatment of cataract, particularly, to the preparations for the prevention and/or treatment of cataract by using 3(2H)-furanone derivatives as their active components. The present invention relates to use of the 3-(2H)-furanone derivatives for the prevention and/or treatment of cataract. The present invention also relates to a novel 3(2H)-furanone derivative.

BACKGROUND OF THE INVENTION

It is known that cataract is caused by the congenital disposition, metabolic disorder, or trauma, and they are further classified into several groups.

At present, in order to prevent and/or treat cataract, various agents such as Pirenoxine ophtalmics, reduced glutathione ophtalmics, sialaden hormone tablets, Thiopronine tablets, vitamines such as vitamin C and E, aldose reductase (AR) inhibitors such as Tolrestat and Epalrestat are clinically employed(Seiji Kumakura, Chemistry and Economy, 11:78–83, 1993). However, these agents do not have enough effects in the cataract treatment.

As pharmaceutical preparations for treating diabetic cataract, a variety of agents which inhibit AR activity have been developed and proposed. Among of such agents, there are the agents containing furanone derivatives having a 2(5H)-furanone skeleton as the mother skeleton as an active component. They are disclosed in the Japanese Published unexamined Patent Application (hereinafter refferred to as "KOKAI") Nos. SHO59-16,884, SHO60-178,879 and SHO61-267,566, and the Japanese Published Examined Patent Application No. HEI8-13,739, and so forth. These agents, the 2(5H)-furanone derivatives disclosed above have enough treatment effects to diabetic cataract; however, they don't have enough effects to senile cataract treatment nor its prevention.

The known preparations for cataract treatment are effective when they are administrated orally, intravenously, or intraperitoneally. Most of them are not effective when they are administrated as ophtalmics.

SUMMARY OF THE INVENTION

The object of the present invention is to provide a pharmaceutical preparation which has enough effects for the prevention and/or treatment of cataract caused by disorder of oxidation, particularly, the pharmaceutical preparation capable of being administrated as the ophtalmics. Other object of the present invention is to provide use of a substance which is more effective for the prevention and/or treatment of cataract. Further object of the present invention is also to provide novel 3(2H)-furanone derivatives.

The present inventors had studied harder, and they found that the furanone derivatives having a 3(2H)-furanone skeleton as a mother skeleton or phramaceutically acceptable salts thereof have enough effect for the prevention and/or treatment of cataract caused by oxidation disorder when they are administrated orally, intravenously, or intraperitoneally. They further found that the furanone derivatives or the pharmaceutically acceptable salts thereof are also effective to the cataract described above when they are administrated as the ophtalmics. Then, they accomplished the present invention.

Firstly, the present invention provides a pharmaceutical preparation for the prevention and/or treatment of cataract comprising a effective amount of a furanone derivative having the 3(2H)-furanone skeleton as the mother skeleton, or a pharmaceutically administrated salt thereof. The furanone derivative is referred to as a 3(2H)-furanone derivative herein below.

The 3(2H)-furanone derivative is preferably a compound shown in formula(1):

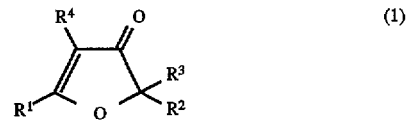

(1)

wherein $R^1$, $R^2$, $R^3$ and $R^4$ are identical or different, independently, and are groups selected from the group consisting of a hydrogen atom, halogen atom, hydroxy group, amino group, mercapto group, carboxy group, carbamoyl group, alkyl group, alkenyl group, alkynyl group, alkoxy group, alkenyloxy group, alkynyloxy group, aryloxy group, aryl group, aralkyl group, arylalkoxy group, acyloxy group and alkoxycarbonyl group.

Secondly, the present invention provides an use of the 3(2H)-furanone derivative or its pharmaceutically acceptable salt with effective dosage, as a pharmaceutical preparation for prevention and/or treatment of cataract.

Thirdly, a method for prevention and/or treatment of cataract which comprises using the 3(2H)-furanone derivative or its pharmaceutically acceptable salt with effective dosage.

Futhermore, the present invention provides a 4-alkoxy-3 (2H)-franone derivative shown in formula(2):

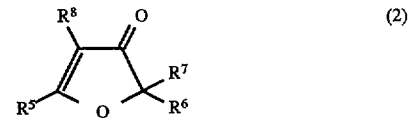

(2)

wherein $R^5$, $R^6$, and $R^7$ are identical or different, independently, and are a hydrogen atom or an alkyl group, and $R^8$ is an alkoxy group.

Furthermore, the present invention provides a 4-acyloxy-3(2H)-furanone derivative shown in formula(3):

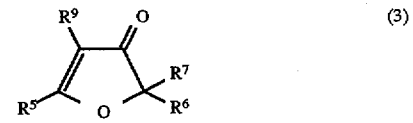

(3)

wherein $R^5$, $R^6$, and $R^7$ are identical or different, independently, and are a hydrogen atom or alkyl group, and at least one of $R^6$ and $R^7$ is a hydrogen atom; and wherein $R^9$ is acyloxy group comprising hydrocarbon part selected from the group consisting of a saturated and unsaturated aliphatic hydrocarbon group having 2 to 22 carbon atoms and an aryl group.

The pharmaceutical preparation of the present invention for the prevention and/or treatment of cataract has improved effect to prevent and/or treat the cataract which is caused by the oxidation disorder. Accordingly, the 3(2H)-furanone derivatives of the present invention show the improved effect to prevent and/or treat senile cataract. Particularly, the preparation of the present invention is capable of being administrated with an enough effect as the ophtalmics.

BRIEF DESCRIPTION OF THE DRAWINGS

FIG. 4 shows the time-dependent changes in the cataract onset rate in the test groups in Experimental Example 8.

FIG. 5 shows the time-dependent changes in the cataract onset rate in the test groups in Experimental Example 9.

FIG. 6 shows the time-dependent changes in the cataract onset rate in the test groups in Comparative Example 2.

DETAILED DESCRIPTION OF THE INVENTION

Figure 1:
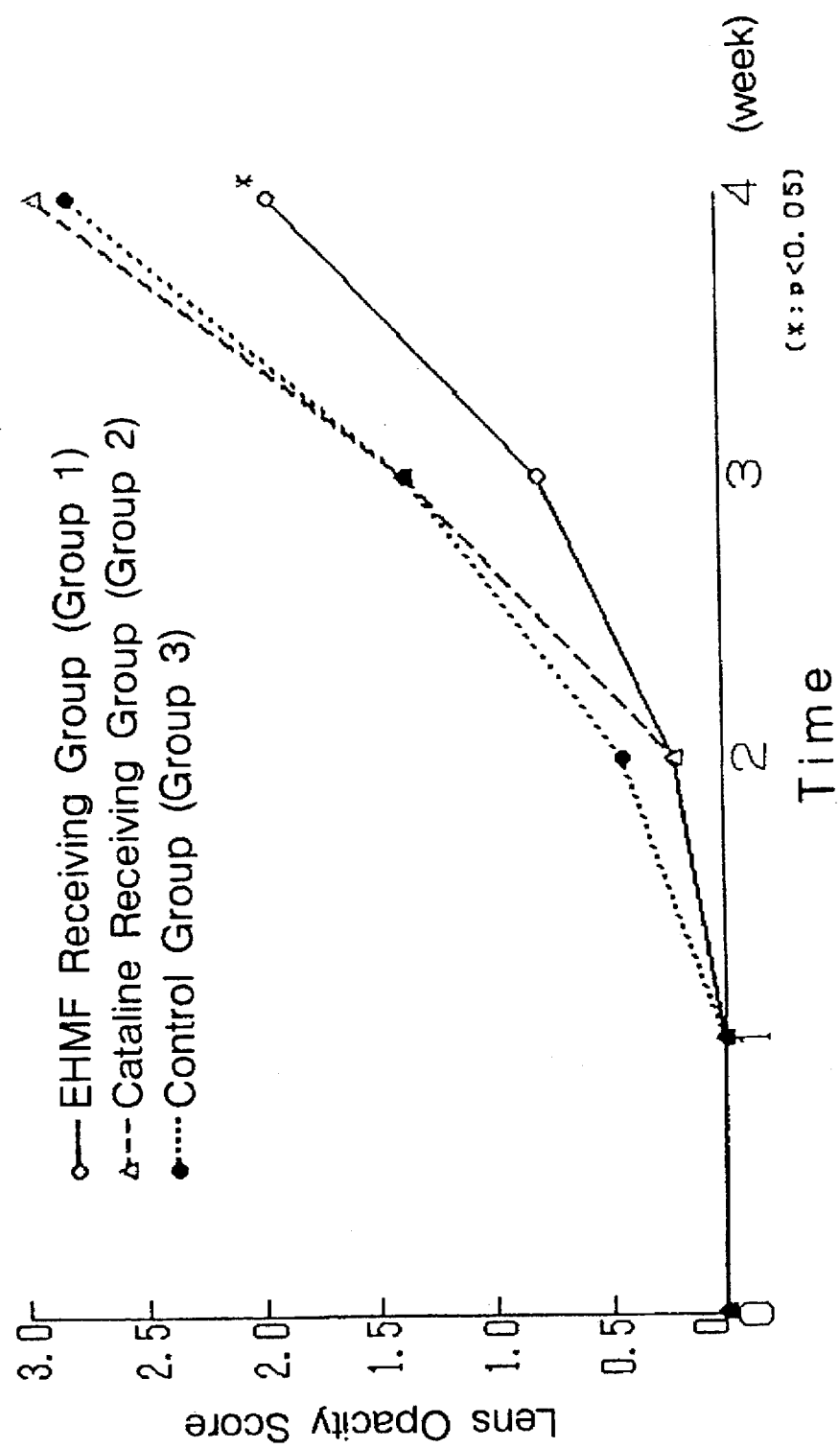
FIG. 1 shows the time-dependent changes in the average scores of lens opacity in the test groups in Experimental Example 2.

The pharmaceutical preparations of the present invention for the prevention and/or treatment of cataract comprises 3(2H)-furanone derivatives or pharmaceutically acceptable salts thereof as their active components. Furthermore, the 3(2H)-furanone derivatives shown in formula (1) are preferable because they show strong prevention and/or treatment effects for cataract, and such effects are sometimes referred to as anti-cataract effect.

$R^1$, $R^2$, $R^3$, and $R^4$ in formula (1) are identical or different, independently, and are groups selected from the group consisting of a hydrogen atom, halogen atom, hydroxy group, amino group, mercapto group, carboxy group, carbamoyl group, alkyl group, alkenyl group, alkynyl group, alkoxy group, alkenyloxy group, alkynyloxy group, aryloxy group, aryl group, aralkyl group, arylalkoxy group, acyloxy group and alkoxycarbonyl group.

The alkyl group may be linear, branched, or cyclic. Such alkyl group has at least one carbon atom, preferably 1 to 6 carbon atoms. Concretely, methyl group, ethyl group, n-propyl group, isopropyl group, isobutyl group, sec-butyl group, n-butyl group, tert-butyl group, n-amyl group, n-hexyl group, or cyclohexyl group are given as examples.

The alkyl group described above may be substituted by any functional group selected from the group consisting of a halogen atom, hydroxy group, amino group, nitro group, mercapto group, sulfonic acid group, carboxy group, phenyl group, aralkyl group, arylalkoxy group, alkoxy group, acyloxy group, carbamoyl group, and alkoxycarbonyl group.

Both the alkenyl and alkynyl groups may be linear, branched, or cyclic. Such alkyl groups have at least two carbon atoms, preferably 2 to 6 carbon atoms. Concretely, vinyl or allyl groups are given as examples of the alkenyl group; ethynyl or propynyl groups are given as those of the alkynyl group. Such alkenyl and alkynyl group may be substituted by the same groups as given for the alkyl group substitution described above.

The alkoxycarbonyl group comprises an alkyl chain which has at least one carbon atom, preferably 1 to 6 carbon atoms. The alkyl chain may be linear, branched, or cyclic. Concretely, methoxycarbonyl, ethoxycarbonyl groups and so forth are given. Such alkyl chains may be substituted by the same functional groups as described in the alkyl group substitution.

The alkoxy group comprises an alkyl chain which has at least one carbon atom, preferably 2 to 22 carbon atoms. The alkyl chain may be linear, branched, or cyclic. Concretely, a methoxy group, ethoxy group, n-propoxy group, isopropoxy group, isobutoxy group, sec-butoxy group, tert-butoxy group, n-pentoxy group, n-hexoxy group, and so forth are given. Such alkyl chain may be substituted by the same functional groups as described in the alkyl group substitution.

Both the alkenyloxy and alkynyloxy groups comprise an alkenyl chain and an alkynyl chain respectively, and may be linear, branched, or cyclic. Such alkenyl and alkynyl chains have at least two carbon atoms, preferably 2 to 22 carbon atoms. Concretely, vinyloxy and allyloxy groups are given as examples of the alkenyloxy group; ethynyloxy and propynyloxy groups are given as those of the alkynyloxy group. Such alkenyloxy and alkynyloxy groups may be substituted by the same functional groups as described in the alkyl group substitution.

As an example of the aryloxy group, an phenoxy group is given. The aryloxy group may be substituted by the same functional groups as described in the alkyl group substitution.

The acyloxy group comprises saturated or unsaturated aliphatic hydrocarbon groups. When the saturated or unsaturated aliphatic hydrocarbon groups are contained in an acyloxy group, these groups have at least one carbon atom, preferably 2 to 22 carbon atoms. The saturated or unsaturated aliphatic hydrocarbon groups may be linear, branched, or cyclic. Concretely, an acetoxy group, pivaloyloxy group, propionyloxy group, butyryloxy group, isobutyryloxy group, valeryloxy group, isovaleryloxy group, n-hexanoyloxy group, n-heptanoyloxy group, n-octanoyloxy group, palmitoyloxy group, n-heptadecanoyloxy, group, stearoyloxy group, oleoyloxy group, linoleoyloxy group, linolenoiloxy group, 4, 7, 10, 13, 16, 19-docosahexaenoyloxy, benzoyloxy group, and so forth are given.

Such aliphatic hydrocarbon groups in the acyloxy group may be substituted by the same functional groups as described in the alkyl group substitution. Concretely, a β-aminopropionyloxy group, γ-aminobutyryloxy group, β-aminoisobutyryloxy group, δ-aminovaleryloxy group, γ-aminoisovaleryloxy group, ε-amino-n-hexanoyloxy group, α-amino-β-mercapto-propionyloxy group, and so forth are given as the examples of such the substitution groups. Both the acetoxy group and pivaloyloxy group are particularly preferable.

As an example of the aryl group, phenyl group is given. The aryl group may be substituted by the same functional groups as shown in the alkyl group substitution.

Both the aralkyl and arylalkoxy groups comprise alkylene moieties which have at least one carbon atom, preferably 1 to 6 carbon atoms. The alkylene moieties described above may be linear, branched, or cyclic. Concretely, a 3-phenylpropyl group and so forth are given as examples of the aralkyl group. A 2-Phenylethoxy group and so forth are given as those of the arylalkoxy group. Such aralkyl and arylalkoxy groups may be substituted by the same functional groups as given for the alkyl group substitution. As examples of an aralkyl group which is substituted, 4-(4'-nitrophenyl)-butyl group and so forth are given. As examples of arylalkoxy group which is substituted, 6-(3', 4'-dichlorophenyl)-hexoxy group and so forth are given.

As active components of the pharmaceutical preparation of the present invention for the prevention and/or treatment for cataract, preferable are the compounds shown in formula (1) in which $R^1$, $R^2$, $R^3$, and $R^4$ are groups selected from the group consisting of a hydrogen atom, hydroxyl group, alkyl group, alkoxy group, and acyloxy group.

The pharmaceutical preparations containing as their active components the 3(2H)-furanone derivatives whose $R^4$ is a group selected from the group consisting of a hydrogen atom, hydroxy group, phenyl group, carboxy group, alkoxycarbonyl group, alkoxy group, and acyloxy group are explained herein below. The production methods of some of the compounds described above are also explained.

(1) A 3(2H)-Furanone Derivative whose $R^4$ is a Hydrogen Atom

As the 3(2H)-furanone derivative whose $R^4$ is a hydrogen atom, bullatenone, 2,2-dimethyl-3(2H)-furanone, (E)-5-(1'-propenyl)- 3(2H)-furanone, 5-vinyl-3(2H)-furanone, 2,5-dimethyl-3(2H)-furanone, and so forth are given. Bullatenone is a 3(2H)-furanone derivative shown in the above formula(1) whose $R^1$ is a phenyl group, both $R^2$ and $R^3$ are methyl groups, and $R^4$ is a hydrogen atom. As one of the other examples, 5-amino-2-alkyl-2-methyl-3(2H)-furanone is also given(cf. Kim. Geterotsikl. Soedin., 9:1286–1287 (1988)).

Such derivatives containing a hydrogen atom at $R^4$ can be synthesized by the known method, for instance, by that of Smith et al.(cf. A. B. Smith III et al., J. Am. Chem. Soc., 103:1501(1981); the Japanese publication application SHO59-20,671). For example, 2,5-dimethyl-3(2H)-furanone is obtained from the following method; 5-acetyltetrahydro-2-hydroxy-2,5-dimethyl-3-oxofurane, which is a dimer of diacetyl produced by aldol condensation, is employed as a starting material, and acetic acid is removed by acid hydrolysis.

(2) A 3(2H)-Furanone Derivative whose $R^4$ is a Hydroxy Group

The franone derivatives whose $R^4$ is a hydroxy group are referred to as 4-hydroxy-3(2H)-furanone derivatives. The 4-hydroxy-3(2H)-furanone derivatives show the tautomerism when the 3(2H)-furanone skeleton has two groups on its position 2, and one of which is a hydrogen atom, and another on the position 2 and a group on the position 5 of the skeleton are different. Concretely, when either $R^2$ or $R^3$ of the 4-hydroxy-3(2H)-furanone derivatives is a hydrogen atom and another symbol is the group except a hydrogen atom, and its group and $R^1$ are different, such derivatives have tautomers existing an equilibrium state.

As examples of the 4-hydroxy-3(2H)-furanone derivatives, the following compounds are given: 2(or 5)-ethyl-4-hydroxy-5(or 2)-methyl-3(2H)-furanone, 4-hydroxy-5(or 2)-methyl-2(or 5)-n-propyl-3(2H)-furanone, 4-hydroxy-2(or 5)-isopropyl-5(or 2)-methyl-3(2H)-furanone, 2(or 5)-n-butyl- 4-hydroxy-5(or 2)-methyl-3(2H)-furanone, 4-hydroxy-2 (or 5)-isobutyl-5(or 2)-methyl-3 (2H)-furanone, 5(or 2)-ethyl-4-hydroxy-2 (or 5)-n-propyl-3 (2H)-furanone, 5(or 2)-ethyl-4-hydroxy-2 (or 5)-isobutyl-3 (2H)-furanone, 4-hydroxy-2, 5-dimethyl-3(2H)-furanone, 2,5-diethyl-4-hydroxy-3(2H)-furanone, 4-hydroxy-3(2H)-furanone, 4-hydroxy-2, 2, 5-trimethyl-3(2H)-furanone, 2, 5-diethyl-4-hydroxy-2 -methyl-3(2H)-furanone, 4-hydroxy-2-(2'-hydroxyethyl)-2, 5-dimethyl-3(2H)-furanone, 4-hydroxy-2-(1'-hydroxyphenyl)-2, 5-dimethyl-3(2H)-furanone, 4-hydroxy-2-(1'-hydroxy-2'-phenylethyl)-2, 5-dimethyl-3(2H)-furanone and so forth.

The 4-Hydroxy-3(2H)-furanone derivatives are synthesized by known synthetic methods. For example, such derivatives are synthesized according to the reaction scheme (4):

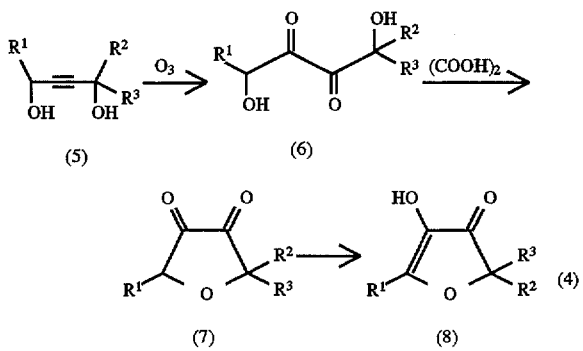

wherein $R^1$, $R^2$ and $R^3$ are the same as described before.

Firstly, the 2-butyne-1,4-diol derivative shown in formula (5) described before is employed as a starting material. The derivative is oxidized by ozone($O_3$) to obtain the compound shown in formula(6) described before. The compound(6) is treated by triphenylphosphine($\phi Ph$) and cyclized by using oxalic acid[$(COOH)_2$] to obtain 4-hydroxy-3(2H)-furanone derivatives via the intermediate shown in formula(7) described before(cf. KOKAI No. SHO49-82,656, the U.S. Pat. No. 3,576,014, the U.S. Pat. No. 3,728,397).

The methods for synthesizing the 4-hydroxy-3(2H)-furanone derivatives in which either $R^2$ or $R^3$ bound to the position 2 of the skeleton is a hydrogen atom and the other is an alkyl group in which at least one hydrogen atom of it is substituted by a functional group selected from the group consisting of a carboxy group, amino group, hydroxy group, and mercapto group are, for instance as follows (cf. the U.S. Pat. Nos. 3,576,014, and 3,728,397).

(2-a) Synthesis of 3(2H)-Furanone Derivatives in which the Alkyl Group is Substituted by a Carboxy Group The 3(2H)-furanone derivatives are synthesized according to reaction scheme(9):

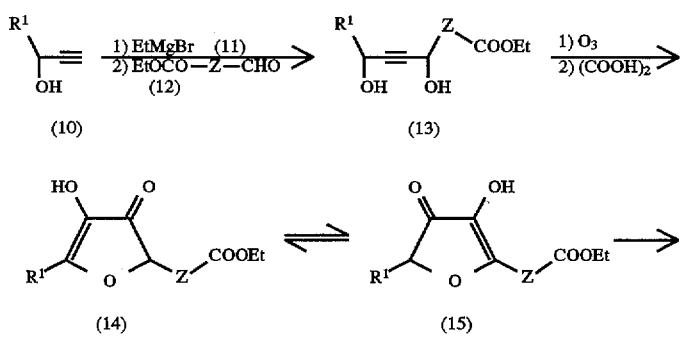

$$\text{(16)} \quad \rightleftharpoons \quad \text{(17)} \quad (9)$$

wherein $R^1$ is the same functional group as described before, Z is an alkylene group, and Et is an abbreviation of an ethyl group.

The propargyl alcohol derivative shown in formula(10) described above is employed as a starting material. The derivative(10) reacts with the Grigniard reagent shown in formula(11) described above, and then reacts with the compound shown in formula(12) described above to form the intermediate shown in formula(13) described above. The intermediate reacts with ozone and then φPh and oxalic acid to form the mixture of tautomers shown in formulae(14) and (15). These compounds are deblocked to form the mixture of desired tautomers shown in formulae(16) and (17).

(2-b) Synthesis of 4-Hydroxy-3(2H)-Furanone Derivatives in which the Alkyl Group is Substituted by an Amino Group, Hydroxy Group, or Mercapto Group The derivatives of (2-b) are synthesized according to the same reaction scheme(9) employed in (2-a) except that the following three compounds are used.

In the derivatives substituted by an amino group;
The compound shown in formula(18) is employed instead of the compounds shown in formula(12).

$$\text{BocNH—Z—CHO} \quad (18)$$

wherein Z is an alkylene group, and Boc shows a tert-butoxycarbonyl group.

In the derivatives substituted by a hydroxy group;
The compound(19) is employed instead of the compounds shown in formula(12).

$$\text{AcO—Z—CHO} \quad (19)$$

wherein Z is an alkylene group, and Ac shows an acetyl group.

In the derivatives substituted by a mercapto group;
The compound(20) is employed instead of the compound shown in the formula(12).

$$\text{AcS—Z—CHO} \quad (20)$$

wherein Z is alkylene group, and Ac shows an acetyl group.

(3) A 3(2H)-Furanone Derivative whose $R^4$ is a Phenyl Group

The furanone derivative in which a phenyl group is bound to the position 4 of the 3(2H)-furanone skeleton is referred to as a 4-phenyl-3(2H)-furanone derivative. For example, 2-methoxy-2, 4-diphenyl-3(2H)-furanone, 2-hydroxy-2, 4-diphenyl-3(2H)-furanone, and so forth are given. 2-hydroxy-2, 4-diphenyl-3(2H)-furanone is commercially obtained from Tokyo Kasei Kogyo(K.K).

(4) A 3(2H)-Furanone Derivative whose $R^4$ is a Carboxy Group

The furanone derivative in which a carboxy group is bound to the position 4 of the 3(2H)-furanone skeleton is referred to as a 4-carboxy-3(2H)-furanone derivative. For example, 4-carboxy-2, 5-dimetyl-3(2H)-furanone, and so forth are given(cf. KOKAI No. SHO49-82,656).

(5) A 3(2H)-Furanone Derivative whose $R^4$ is an Alkoxycarbonyl Group

The furanone derivative in which an alkoxycarbonyl group is bound to the position 4 of the 3(2H)-furanone skeleton is referred to as a 4-alkoxycarbonyl-3(2H)-furanone derivative. For example, 4-ethoxycarbonyl-2, 5-dimethyl-3(2H)-furanone, 4-ethoxycarbonyl-2-n-hexyl-5-methyl-3(2H)-furanone, 4-ethoxycarbonyl-2-methyl-5-n-propyl-3(2H)-furanone, and so forth are given(cf. KOKAI No. SHO49-82,656).

(6) A 3(2H)-Furanone Derivative whose $R^4$ is an Alkoxy Group

The furanone derivative in which an alkoxy group is bound to the position 4 of the 3(2H)-furanone skeleton is referred to as a 4-alkoxy-3(2H)-furanone derivative.

Among the compounds shown in formula(1), the 4-alkoxy-3(2H)-furanone derivatives shown in formula(2) are the novel compounds synthesized by the present inventors.

As examples of 4-alkoxy-3(2H)-furanone derivatives, a variety of compounds are given: 2-ehtyl-4-methoxy-5-methyl-3(2H)-furanone, 5-ethyl-4-methoxy-2-methyl-3(2H)-furanone, 4-ethoxy-2-ethyl-5-methyl-3(2H)-furanone, 4-ethoxy-5-ethyl-2-methyl-3(2H)-furanone, 2-ethyl-5-methyl-4-propoxy-3(2H)-furanone, 5-ethyl-2-methyl-4-propoxy-3(2H)-furanone, 2-ethyl-4-isopropoxy-5-methyl-3(2H)-furanone, 5-ethyl-4-isopropoxy-2-methyl-3(2H)-furanone, 4-butoxy-2-ethyl-5-methyl-3(2H)-furanone, 4-butoxy-5-ethyl-2-methyl-3(2H)-furanone, 2-ethyl-4-isobutoxy-5-methyl-3(2H)-furanone, 5-ethyl-4-isobutoxy-2-methyl-3(2H)-furanone, 4-sec-butoxy-2-ethyl-5-methyl-3(2H)-furanone, 4-sec-butoxy-5-ethyl-2-methyl-3(2H)-furanone, 4-tert-butoxy-2-ethyl-5-methyl-3(2H)-furanone, 4-tert-butoxy-5-ethyl-2-methyl-3(2H)-furanone, 2-ethyl-5-methyl-4-n-pentoxy-3(2H)-furanone, 5-ethyl-2-methyl-4-n-pentoxy-3(2H)-furanone, 2-ethyl-4-n-hexoxy-5-methyl-3(2H)-furanone, 5-ethyl-4-n-hexoxy-2-methyl-3(2H)-furanone, 2-ethyl-4-methoxy-2, 5-dimethyl-3(2H)-furanone, 5-ethyl-4-methoxy-2, 2-dimethyl-3(2H)-furanone, 4-ethoxy-2, 2-diethyl-5-methyl-3(2H)-furanone, 4-ethoxy-2, 5-diethyl-2-methyl-3(2H)-furanone, 2-ethyl-5-methyl-4-propoxy-2-propyl-3(2H)-furanone, 5-ethyl-2-methyl-4-propoxy-2-propyl-3(2H)-furanone, 2-ethyl-4-isopropoxy-2-isopropyl-5-methyl-3(2H)-furanone, 5-ethyl-4-isopropoxy-2-isopropyl-2-methyl-3(2H)-furanone, 4-n-butoxy-2-n-butyl-2-ethyl-5-methyl-3(2H)-furanone, 2-ethyl-4-isobutoxy-2-isobutyl-5-methyl-3(2H)-furanone, 5-ethyl-4-isobutoxy-2-isobutyl-2-methyl-3(2H)-furanone, 4-sec-butoxy-2-sec-butyl-2-ethyl-5-methyl-3(2H)-furanone, 4-sec-butoxy-2-sec-butyl-5-ethyl-2-methyl-3(2H)-furanone, 4-tert-butoxy-2-tert-butyl-2-ethyl-5-methyl-3(2H)-furanone, 4-tert-butoxy-2-tert-butyl-5-ethyl-2-methyl-3(2H)-furanone, 2-ethyl-5-methyl-4-n-pentoxy-2-n-pentyl-3(2H)-furanone, 5-ethyl-2-methyl-4-n-pentoxy-2-n-pentyl-3(2H)-furanone, 2-ethyl-4-isopentoxy-2-isopentyl-5-methyl-3(2H)-furanone, 5-ethyl-4-isopentoxy-2-isopentyl-2-methyl-3(2H)-furanone, 2-ethyl-4-n-hexoxy-2-n-hexyl-5-methyl-3(2H)-furanone, 5-ethyl-4-n-hexoxy-2-n-hexyl-2-methyl-3(2H)-furanone and so forth.

The 4-Alkoxy-3(2H)-furanone derivatives are synthesized by reacting the 4-hydroxy-3(2H)-furanone derivatives with alkyl halide shown in formula(21) in the presence of reactive alkaline metal compounds:

$$A—X \quad (21)$$

wherein A is an alkyl group having at least one carbon atom, preferably 2 to 22 carbon atoms; X is an halogen atom. However, the synthetic methods of the derivatives are not limited to the above-mentioned method.

As examples of alkyl halide, methyl iodide, methyl bromide, ethyl iodide, ethyl bromide, propyl iodide, propyl bromide, propyl chloride, isopropyl iodide, isopropyl bromide, isopropyl chloride, butyl iodide, butyl bromide, butyl chloride and so forth are given.

As examples of the reactive alkaline metal compound employed in the above-mentioned reaction, potassium hydride, sodium hydride, sodium hydroxide and so forth are given.

The reaction described above is performed as follows. Firstly, the 4-hydroxy-3(2H)-furanone derivative as starting material is dissolved into a suitable solvent, and subsequently the reactive alkaline metal compound is added. Then, alkyl halide in the suitable solvent or by itself is added into the mixture. The temperature of the reaction is elevated up to any level reaching the boiling point of the solvent to promote the reaction, if desired.

Any solvent in the above reaction may be used unless it is active in the reaction. In general, aromatic hydrocarbons such as benzene, toluene, and xylene; amido compounds, for instance, dimethyl formamide; organic solvents conveniently used in etherification such as dimethyl sulfoxide and tetrahydrofuran and so forth are given. When basic catalysts, for instance, pyridine is employed, such catalysts may be used also as the solvent.

After finishing the reaction, the objective substance, the 4-alkoxy-3(2H)-furanone derivative, is isolated and purified from the reaction mixture obtained. Such isolation and purification are performed by using known methods such as distillation, solvent extraction, fractional crystallization, column chromatography, and liquid chromatography.

During the reaction, the hydrogen atom of the hydroxy group located at the position 4 of the 3(2H)-furanone skeleton is replaced by an alkyl group. When the mixture of tautomers of the derivatives is used as the 4-hydroxy-3(2H)-furanone derivative, the corresponding derivatives in which the hydrogen atoms of the hydroxy groups at the position 4 of the skeletons are replaced by the alkyl groups are obtained.

When the 4-hydroxy-3(2H)-furanone derivative has a hydrogen atoms at the position 2 of the 3(2H)-furanone skeleton and is employed in the above-mentioned reaction as a starting material, the product obtained may be a 2-alkyl derivative of the starting material, because the hydrogen atom may be replaced by alkyl group.

The 4-Alkoxy-3(2H)-furanone derivatives obtained above are identified by using mass, IR, NMR spectra.

The 4-Alkoxy-3(2H)-furanone derivatives are also produced by using other methods. For instance, such derivatives are obtained by the reaction of the 4-hydroxy-3(2H)-furanone derivatives in which the hydroxy group at the position 4 is substituted by metal such as sodium and potassium with either dialkyl sulfate or alkyl ester of aryl sulfate; by the dehydration of the 4-alkoxy-3(2H)-furanone derivatives with alcohols; by the methylation of the 4-hydroxy-3(2H)-furanone derivatives with diazomethane, and so forth.

(7) A 3(2H)-Furanone Derivative whose $R^4$ is an Acyloxy Group

The 3(2H)-Furanone derivative having an acyloxy group at the position 4 of the 3(2H)-furanone skeleton is referred to as a 4-acyloxy- 3(2H)-furanone derivative.

Among the 4-acyloxy-3(2H)-furanone derivatives shown in formula(1) described above, the derivatives having a hydrogen atom on either $R^2$ or $R^3$ bound to the position 2 of the 3(2H)-furanone skeleton and having other groups except a hydrogen atom on another are preferable. As a concrete example, 4-acetoxy-2-ethyl-5-methyl-3(2H)-furanone is known.

Furthermore, the 4-acyloxy-3(2H)-furanone derivatives shown in formula(3) are novel compounds synthesized by the inventors of the present invention.

As examples of 4-acyloxy-3(2H)-furanone derivatives, the following compounds are given: 2-ethyl-5-methyl-4-propionyloxy-3(2H)-furanone, 5-ethyl-2-methyl-4-propionyloxy-3(2H)-furanone, 4-butyryloxy-2-ethyl-5-methyl-3(2H)-furanone, 4-butyryloxy-5-ethyl-2-methyl-3(2H)-furanone, 2-ethyl-4-isobutyryloxy-5-methyl-3(2H)-furanone, 5-ethyl-4-isobutyryloxy-2-methyl-3(2H)-furanone, 2-ethyl-5-methyl-4-valeryloxy-3(2H)-furanone, 5-ethyl-2-methyl-4-valeryloxy-3(2H)-furanone, 2-ethyl-4-isovaleryloxy-5-methyl-3(2H)-furanone, 5-ethyl-4-isovaleryloxy-2-methyl-3(2H)-furanone, 2-ethyl-4-n-hexanoyloxy-5-methyl-3(2H)-furanone, 5-ethyl-4-n-hexanoyloxy-2-methyl-3(2H)-furanone, 2-ethyl-4-n-heptanoyloxy-5-methyl-3(2H)-furanone, 5-ethyl-4-n-heptanoyloxy-2-methyl-3(2H)-furanone, 2-ethyl-5-methyl-4-n-octanoyloxy-3(2H)-furanone, 5-ethyl-2-methyl-4-n-octanoyloxy-3(2H)-furanone, 2-ethyl-5-methyl-4-n-nonanoyloxy-3(2H)-furanone, 5-ethyl-2-methyl-4-n-nonanoyl-3(2H)-furanone, 4-n-decanoyloxy-2-ethyl-5-methyl-3(2H)-furanone, 4-n-decanoyloxy-5-ethyl-2-methyl-3(2H)-furanone, 2-ethyl-5-methyl-4-n-undecanoyloxy-3(2H)-furanone, 5-ethyl-2-methyl-4-n-undecanoyloxy-3(2H)-furanone, 4-n-dodecanoyloxy-2-ethyl-5-methyl-3(2H)-furanone, 4-n-dodecanoyloxy-5-ethyl-2-methyl-3(2H)-furanone, 2-ethyl-5-methyl-4-n-tridecanoyloxy-3(2H)-furanone, 5-ethyl-2-methyl-4-n-tridecanoyloxy-3(2H)-furanone, 2-ethyl-5-methyl-4-n-tetradecanoyloxy- 3(2H)-furanone, 5-ethyl-2-methyl-4-n-tetradecanoyloxy-3(2H)-furanone, 2-ethyl-5-methyl-4-n-pentadecanoyl-3(2H)-furanone, 5-ethyl-2-methyl-4-n-pentadecanoyloxy-3(2H)-furanone, 2-ethyl-5-methyl-4-palmitoyloxy-3(2H)-furanone, 5-ethyl-2-methyl-4-palmitoyloxy-3(2H)-furanone, 2-ethyl-4-n-heptadecanoyl-5-methyl-3(2H)-furanone, 5-ethyl-4-n-heptadecanoyloxy-2-methyl-3(2H)-furanone, 2-ethyl-5-methyl-4-stearoyloxy-3(2H)-furanone, 5-ethyl-2-methyl-4-stearoyloxy-3(2H)-furanone, 2-ethyl-5-methyl-4-oleoyloxy-3(2H)-furanone, 5-ethyl-2-methyl-4-oleoyloxy-3(2H)-furanone, 2-ethyl-4-linoleoyloxy-5-methyl-3(2H)-furanone, 5-ethyl-4-linoleoyloxy-2-methyl-3(2H)-furanone, 2-ethyl-5-methyl-4-n-nonadecanoyloxy-3(2H)-furanone, 5-ethyl-2-methyl-4-n-nonadecanoyloxy-3(2H)-furanone, 4-n-eicosanoyloxy-2-ethyl-5-methyl-3(2H)-furanone, 4-n-eicosanoyloxy-5-ethyl-2-methyl-3(2H)-furanone, 2-ethyl-4-n-heneicosanoyloxy-5-methyl-3(2H)-furanone, 5-ethyl-4-n-heneicosanoyloxy-2-methyl-3(2H)-furanone, 4-n-docosanoyloxy-2-ethyl-5-methyl-3(2H)-furanone, 4-n-docosanoyloxy-5-ethyl-2-methyl-3(2H)-furanone, 4-(4, 7, 10, 13, 16, 19-docosahexaenoyloxy)-2-ethyl-5-metyl-3(2H)-furanone, 4-(4, 7, 10, 13, 16, 19-docosahexaenoyloxy)-5-ethyl-2-metyl-3(2H)-furanone, 2-ethyl-5-methyl-4-n-tricosanoyloxy-3(2H)-furanone, 5-ethyl-2-methyl-4-n- tricosanoyloxy-3(2H)-furanone, 2-ethyl-5-methyl-4-n-tetracosanoyloxy-3(2H)-furanone, 5-ethyl-2-methyl-4-n-tetracosanoyloxy-3(2H)-furanone, 2-ethyl-5-methyl-4-n-pentacosanoyloxy-3(2H)-furanone, 5-ethyl-2-methyl-4-n-pentacosanoyloxy-3(2H)-furanone, 4-β-aminopropionyloxy-2-ethyl-5-methyl-3(2H)-furanone, 4-β-aminopropionyloxy-5-ethyl-2-methyl-3(2H)-furanone, 4-γ-aminobutyryloxy-2-ethyl-5-methyl-3(2H)-furanone, 4-γ-aminobutyryloxy-5-ethyl-2-methyl-3(2H)-furanone, 4-β-aminoisobutyryloxy-2-ethyl-5-methyl-3(2H)-furanone, 4-β-aminoisobutyryloxy-5-ethyl-2-methyl-3(2H)-furanone, 4-δ-aminovaleryloxy-2-ethyl-5-methyl-3(2H)-furanone, 4-δ-aminovaleryloxy-5-ethyl-2-methyl-3(2H)-furanone, 4-γ-aminoisovaleryloxy-2-ethyl-5-methyl-3(2H)-furanone, 4-γ-aminoisovaleryloxy-5-ethyl-2-methyl-3(2H)-furanone, 4-(ε-amino-n-hexanoyloxy)-2-ethyl-5-methyl-3(2H)-furanone, 4-(ε-amino-n-hexanoyloxy)-5-ethyl-2-methyl-3(2H)-furanone, and so forth.

The derivatives of 4-acyloxy-3(2H)-furanone are synthesized by using the 4-hydroxy-3(2H)-furanone derivatives described above and carboxylic acids shown in formula(22):

B—COOH    (22)

wherein, B represents an aryl group, saturated aliphatic hydrocarbon group, or unsaturated hydrocarbon group. As the compounds of formula(22), acid halide, acid anhydride, reactive ester and so forth may be used (cf. KOKAI No. SHO-49-82,656).

As concrete examples of the carboxylic acid shown in the above-mentioned formula(22), the following compounds are given: propionic acid, butyric acid, isobutyric acid, valeric acid, isovaleric acid, perargonic acid, caprylic acid, palmitic acid, stearic acid, vinyl acetate, pentenoic acid, pivalic acid, 2-hexenoic acid, 2-methyl-2-pentenoic acid, 3-methyl-2-pentenoic acid, 2-heptenoic acid, 2-octenoic acid, 4-dodecenoic acid, 4-tetradecenoic acid, oleic acid, 2, 4-hexadienoic acid, 9, 12-octadecadienoic acid, 2, 4, 6-octatrienoic acid, linoleic acid, arachidonic acid, docosahexaenoic acid, β-aminopropionic acid, γ-aminobutyric acid, β-aminoisobutyric acid, δ-aminovaleric acid, γ-aminoisovaleric acid, ε-amino-n-hexanoic acid, and so forth. In addition, amino acids such as cysteine, methionine, serine, and glutamic acid are given.

Although such carboxylic acids as described above may be used as free acids, they can be in general used as the forms of acid halide, acid anhydride, and so forth.

When the above-mentioned carboxylic acid is reacted with the compounds as free acid, it is preferable to employ acid catalysts such as p-toluenesulfonic acid, sulfuric acid, acidic ion-exchange resin, or desiccants such as dicyclohexylcarbodiimido, trifluoroacetic anhydride, magnesium sulfate anhydride, molecular sieve 5A, and polyphosphoric acid.

When the above-mentioned carboxylic acid is reacted with the compounds as the forms of acid halide such as acid chloride and acid bromide, it is beneficial to employ them in the presence of the basic compounds such as pyridine, lutidine, dimethylamino pyridine, dimethylaniline, trimethylamine, tetramethyl urea, diisopropylethylamine, and N-ethylpiperidine.

As other approaches, instead of the above-mentioned carboxylic acids or derivatives thereof, carboxylic acid anhydrides formed from two carboxylic acids, the mixed acid anhydride formed from one of the above-mentioned carboxylic acid and one of other carboxylic acids such as ethyl chlorocarbonate, and isobutyl chloroformate may be employed; such acid anhydrides can react in the presence of the above-mentioned basic compounds, for instance, pyridine. In the reaction, the compounds such as sulfuric acid, zinc chloride, sodium acetate, perchloric acid may be employed as catalysts. Furthermore, the reaction is performed by using lower ester such as methyl ester, ethyl ester, isopropenyl ester with catalysts such as sulfuric acid or p-toluenesulfonic acid.

The above-mentioned reaction is performed as follows. In general, starting compounds, 4-hydroxy-3(2H)-furanone derivatives, are preferably dissolved into solvents, and subsequently catalysts are added, if desirable. Then, the carboxylic acids or the reactive derivatives thereof are gradually added with stirring into the solution containing starting compounds. The reaction is promoted by heating at any temperature lower than a boiling temperature of the solvent.

Any solvent conventionally used in esterification may be employed in the reaction. For example, aryl hydrocarbons such as benzene, toluene, and xylene; halogenated hydrocarbons such as methylene chloride, chloroform, and carbon tetrahydrochloride; amides such as dimethylformamide, and diethylacetamide are given.

After the reaction, the object compound, the 4-acyloxy-3(2H)-furanone derivatives are isolated and purified from the reaction mixture obtained. The conventional method such as distillation, solvent extraction, fractional crystallization, column chromatography, and liquid chromatography may be employed.

In the above-mentioned reaction, a hydrogen atom of the hydroxy groups bound to the position 4 of the 3(2H)-furanone skeleton of 4-hydroxy-3(2H)-furanone derivative is substituted with an acyloxy group. When the mixture of tautomers is employed of the 4-hydroxy-3(2H)-furanone derivative, the hydrogen atoms described before are substituted with an acyloxy group and corresponding tautomers are obtained.

The 4-hydroxy-3(2H)-furanone derivatives obtained are identified by using mass spectrometry, IR, NMR, and so forth.

The 4-Acyloxy-3(2H)-furanone derivatives may be converted into salts thereof. This conversion is performed by means of the conventional salt formation. For example, the salt of the derivative is formed by using carboxy groups of the compounds shown in formula(17) and base such as sodium hydroxide.

The synthetic method of several kinds of the 3(2H)-furanone derivatives are shown hereinbefore, and other methods also are available for synthesizing them. Some methods are shown hereinbelow.

1) Synthesis of 2, 2-dimethyl-4-ehoxycarbonyl-5-(E)-styryl-3(2H)-furanone by using 5-methyl-3(2H)-furanone and Schiff base(cf. Synthesis, 1:45–47(1981))

2) Synthesis of dialkoxydiepoxyalkane-4-hydroxy-3(2H)-furanone from α,α'-dibromo-1,2-dione in the presence of sodium alkoxide(cf. Synthesis, 9:709(1981))

3) Synthesis of 4, 5-dihydro-3(2H)-furanone from 2-butyne-1, 4-diol derivatives by means of regio-controlled hydration(cf. J. Am. Chem. Soc., 103:4975–4977(1981))

4) Production of 3(2H)-furanone derivatives from $\Delta^2$-isoxazolines by means of reduction(cf. Tetrahedron Letters, 24:2079–2082(1983))

5) Synthesis of dihydro-3(2H)-furanone from 1, 3-dithiane as starting derivative(cf. Tetrahedron Letters, 25:5567–5570(1984))

6) Synthesis of 3(2H)-furanone from 5-substitutes-3-isoxazolyl ethyl carboxylate as starting material(cf. Tetrahedron letters, 25:4313–4316(1984))

7) Synthesis of 3(2H)-furanone from 5-aryl-4, 5-dibromo-2-methyl-1, 2-epoxy-pentane-3-one by means of dehydrobromination(cf. Zh. Org. Khim., 21:1330–1334 (1985))

8) Synthesis of 5-aryl-2, 2-dimethyl-3(2H)-furanone derivatives by means of condensation of aryl aldehyde and 3-hydroxy-3-methyl-2-butanone, bromination (addition of bromine atoms), and alkaline treatment of resulting compounds(cf. J. Heterocycl. Chem., 23:1199–1201(1986))

9) Synthesis either 2-acetylmethyl-5-methyl-3(2H)-furanone or 2-acetylmthyl-5-phenyl-3(2H)-furanone from 2-acetylmethyl-5-methylfurane or 2-benzoymethyl-5-methylfurane(cf. Tetrahedron Letters, 28:2297–2298(1987))

10) Synthesis of 3(2H)-furanone derivatives from propargyl alcohol, CO, and halogenated benzene(cf. Chem. Lette., 1:81–82(1988))

11) Synthesis of 3(2H)-furanone derivatives from 5-arylfurane-2, 3 -diones and acylmethylenetriphenylphoaphorane(cf. Pharmazie, 48:99–106(1993))

The 3(2H)-Furanone derivatives produced by using the above-mentioned method also may be preferably used for the pharmaceutical preparations of the present invention for the prevention and/or treatment of cataract.

The pharmaceutical preparations may contain only one of the 3(2H)-furanone derivatives or the mixture of them. Among the above 3(2H)-furanone derivatives, 2, 5-dimethyl-4-pivaloyloxy-3(2H)-furanone, 2-ethyl-5-methyl-4-pivaloyloxy-3(2H)-furanone, 5-ethyl-2-methyl-4-pivaloyloxy-3(2H)-furanone, 4-bytyryloxy-2-ethyl-5-methyl-3(2H)-furanone, 4-acetoxy-2-ethyl-5-methyl-3(2H)-furanone, 4-ethoxy-2-ethyl-5-methyl-3(2H)-furanone, 2-ethyl-4-linoleoyloxy-5-methyl-3(2H)-furanone, 4-hydroxy-2, 5-dimethyl-3(2H)-furanone, 2-ethyl-4-hydroxy-5-methyl-3(2H)-furanone, and 5-ethyl-4-hydroxy-2-methyl-3(2H)-furanone are preferable.

Particularly, 2, 5-dimethyl-4-pivaloyloxy-3(2H)-furanone, 2-ethyl-5-methyl-4-pivaloyloxy-3(2H)-furanone, 5-ethyl-2-methyl-4-pivaloyloxy-3(2H)-furanone, and 4-hydroxy-2, 5-dimethyl-3(2H)-furanone are preferable.

Pharmaceutically acceptable salts of the 3(2H)-furanone derivatives described above are also employed as the pharmaceutical preparations. For instance, alkaline metal salts such as sodium salts and potassium salts; alkaline earth metal salts such as calcium salts; amine salts such as ethanol amine salts, triethylamine salts, dicyclohexylamine salts; ammonium salts are given.

Since the 3(2H)-furanone derivatives have extremely inhibitory activities for oxidation, it is thought that they inhibit excessive oxidation in lens of the eyes.

Such the 3(2H)-furanone derivatives do not inhibit AR activity, however, it is effective for the prevention or treatment of senile cataract caused by oxidation disorder.

The pharmaceutical preparations show excellent effects when they are administrated via any route, for example, p.o., i.v., or i.p. Furthermore, the preparations have good treatment effects for cataract when they are administrated as ophtalmics.

Accordingly, the pharmaceutical preparations are different from the conventional pharmaceutical preparations for cataract treatment which comprises the furanone derivatives having a 2(5H)-furanone skeleton as a mother skelton, which derivatives are AR inhibitors.

The pharmaceutical preparations is administrated orally or parenterally to prevent and/or treat cataract caused by oxidation disorder, for instance, senile cataract.

The pharmaceutical preparations are formulated to any kind of formulation, for example, solid preparations such as tablets, granules, and capsules; liquid preparations such as ophtalmics; injectables by using conventional methods. Such formulations may contain vehicles such as binders, disintegrators, thickeners, emulsifiers, resorptioners, corrigents, buffering agents, surfactants, solubilizing agents, preservatives, suspending agents, isotonicities, stabilizers, and pH adjusting agents.

The dose of the formulations depends on several conditions such as the kind of derivatives; ages and weight of patients; formulations of the preparations, and indications. However, in injectables, 0.01 to 1,000 mg/day per adult is preferable, more preferably 0.1–100 mg/day per adult. In oral administration, the formulations are administrated in several times per day with 0.1–1,000 mg per each time for adult, more preferable 1–1,000 mg. In ophtalmics, the concentration of the ophtalmics is preferably 0.01–10%, more preferably 0.5–2%. One or two drops of the ophtalmics are administrated to patients' eyes in 1–5 times per day, preferably 2–5 times per day.

The pharmaceutical preparations for the prevention or treatment of cataract may contain the above-mentioned furanone derivatives with other components having pharmacological effects.

EXAMPLES

Preparation Example 1

Synthesis of 2,5-Dimethyl-4-Pivaloyloxy-3(2H)-Furanone

4-Hydroxy-2,5-dimethyl-3(2H)-furanone (1.0 g, TOKYO KASEI KOGYO CO., LTD.) and 4-dimethylaminopyridine (0.05 g) were dissolved in a mixture solution of pyridine (10 ml) and methylene chloride (10 ml) under an argon stream in a 50 ml two-necked flask. To the resulting solution, pivaloyl chloride (1.06 ml) was added dropwise under cooling with ice and the mixture was stirred at room temperature for 1 hour. Subsequently, the reaction mixture solution was mixed with a 0.5N ice-cooled aqueous solution of HCl (10 ml) and subjected to extraction with diethyl ether (30 ml). The ether-extraction was repeated 3 times. The ether layer was washed 3 times with a 0.5N aqueous solution of HCl, twice with a saturated aqueous solution of sodium bicarbonate and once with a saturated saline solution and dried over sodium sulfate. The ether layer was then concentrated under a reduced pressure and applied to a silica gel column for separation and purification. Thus, 2,5-dimethyl-4-pivaloyloxy-3(2H)-furanone (1.40 g) was obtained.

(a) Characteristic properties: Colorless oil (b) IR spectrum $v_{max}$ (cm$^{-1}$, film): 2980, 1760, 1720, 1640, 1480, 1410, 1310, 1270, 1190, 1140, 1100, 1030 and 1000 (c) $^1$H-NMR spectrum δ (ppm in CDCl$_3$): 1.32 (s, 9H), 1.49 (d, J=7.3 Hz, 3H), 2.13 (s, 3H), 4.56 (q, J=7.3 Hz, 1H)

Preparation Example 2

Synthesis of 2-Ethyl-5-Methyl-4-Pivaloyloxy-3(2H)-Furanone

2(or 5)-Ethyl-4-hydroxy-5(or 2)-methyl-3(2H)-furanone (1.0 g, TOKYO KASEI KOGYO CO., LTD.) and 4-dimethylaminopyridine (0.05 g) were dissolved in a mixture solution of pyridine (10 ml) and methylene chloride (10 ml) under an argon stream in a 50 ml two-necked flask. To the resulting solution, pivaloyl chloride (0.95 ml) was added dropwise under cooling with ice and the mixture was stirred at room temperature for 1 hour. Subsequently, the reaction mixture solution was mixed with a 0.5N ice-cooled aqueous solution of HCl (10 ml) and subjected to extraction with diethyl ether (30 ml). The ether-extraction was repeated 3 times. The ether layer was washed 3 times with a 0.5N aqueous solution of HCl, twice with a saturated aqueous solution of sodium bicarbonate and once with a saturated saline solution and dried over sodium sulfate. The ether layer was then concentrated under a reduced pressure and applied to a silica gel column for separation and purification. Thus, 2-ethyl-5-methyl-4-pivaloyloxy-3(2H)-furanone (1.30 g) was obtained.

(a) Characteristic properties: Colorless oil (b) IR spectrum $v_{max}$ (cm$^{-1}$, film): 3000, 1770, 1730, 1650, 1490, 1460, 1420, 1320, 1280, 1200, 1110 and 1140 (c) $^1$H-NMR spectrum δ (ppm in CDCl$_3$): 1.01 (t, J=7.3 Hz, 3H), 1.33 (s, 9H), 1.79–2.04 (m, 2H), 2.15 (s, 3H), 4.46 (t, J=5.7 Hz, 1H)

Preparation Example 3

Synthesis of 4-Acetoxy-2-Ethyl-5-Methyl-3(2H)-Furanone (Major) and 4-Acetoxy-5-Ethyl-2-Methyl-3(2H)-Furanone (Minor)

A mixture (1.08 g) of 4-acetoxy-2-ethyl-5-methyl-3(2H)-furanone (major) and 4-acetoxy-5-ethyl-2-methyl-3(2H)-furanone (minor) was obtained by the same method as in Preparation Example 2 except that 0.54 ml of acetyl chloride was used rather than 0.95 ml of pivaloyl chloride.

(a) Characteristic properties: Colorless oil (b) IR spectrum $v_{max}$ (cm$^{-1}$, film): 2980, 1780, 1710, 1630, 1420, 1370, 1320 and 1190 (c) $^1$H-NMR spectrum δ (ppm in CDCl$_3$): 1.01 (t, J=7.5 Hz, 3H) (major), 1.22 (t, J=7.5 Hz, 3H) (minor), 1.45 (d, J=7.5 Hz, 3H) (minor), 1.80–2.04 (m, 2H) (major), 2.18 (s, 3H) (major), 2.27 (s, 3H), 2.65 (q, J=7.5 Hz, 2H) (minor), 4.47–4.53 (1H, m)

Preparation Example 4

Synthesis of 4-Butyryloxy-2-Ethyl-5-Methyl-3(2H)-Furanone (Major) and 4-Butyryloxy-5-Ethyl-2-Methyl-3(2H)-Furanone (Minor)

2(or 5)-Ethyl-4-hydroxy-5(or 2)-methyl-3(2H)-furanone (1.0 g) and 4-dimethylaminopyridine (0.05 g) were dissolved in a mixture solution of pyridine (10 ml) and methylene chloride (10 ml) under an argon stream in a 50 ml two-necked flask. To the resulting solution, butyric anhydride (1.26 ml) was added dropwise under cooling with ice and the mixture was stirred at room temperature for 12 hours. The reaction mixture solution was mixed with a 0.5N ice-cooled aqueous solution of HCl (10 ml) and subjected to extraction with diethyl ether (30 ml). The ether-extraction was repeated 3 times. The ether layer was washed 3 times with a 0.5N aqueous solution of HCl twice with a saturated aqueous solution of sodium bicarbonate and once with a saturated saline solution and dried over sodium sulfate. The ether layer was then concentrated under a reduced pressure and applied to a silica gel column for separation and purification. Thus, a mixture (1.28 g) of 4-butyryloxy-2-ethyl-5-methyl-3(2H)-furanone (major) and 4-butyryloxy-5-ethyl-2-methyl-3(2H)-furanone (minor) was obtained.

(a) Characteristic properties: Colorless oil (b) IR spectrum $v_{max}$ (cm$^{-1}$, film): 2980, 1760, 1710, 1630, 1420, 1320, 1190 and 1130 (c) $^1$H-NMR spectrum δ (ppm in CDCl$_3$): 1.00 (t, J=7.6 Hz, 3H), 1.00 (t, J=7.6 Hz, 3H) (major), 1.21 (t, J=7.6 Hz, 3H) (minor), 1.42–1.97 (m, 2H), 1.49 (d, J=7.0 Hz, 3H) (minor), 1.70–2.00 (m, 2H) (major), 2.16 (s, 3H) (major), 2.35–2.60 (m, 2H) (minor), 2.44–2.60 (m, 2H), 4.40–4.60 (m, 1H)

Preparation Example 5

Synthesis of 2-Ethyl-4-Linoleoyloxy-5-Methyl-3(2H)-Furanone (Major) and 5-Ethyl-4-Linoleoyloxy-2-Methyl-3 (2H)-Furanone (Minor)

2 (or 5)-Ethyl-4-hydroxy-5 (or 2)-methyl-3(2H)-furanone (1.0 g), 4-dimethylaminopyridine (0.05 g) and linoleic acid (1.97 g) were dissolved in methylene chloride (30 ml) under an argon stream in a 50 ml two-necked flask. To the resulting solution, dicyclohexylcarbodiimide (1.80 g) was added at 0° C. and the mixture was stirred at room temperature for 12 hours. The precipitate formed in the reaction mixture solution was then filtered and washed 3 times with methylene chloride. The resulting filtrate and the washing solution were combined. The combined solution was washed sequentially with a 0.5N aqueous solution of HCl a saturated aqueous solution of sodium bicarbonate and a saturated saline solution and dried over sodium sulfate. The solution was then concentrated under a reduced pressure and applied to a silica gel column for separation and purification. Thus, a mixture (2.55 g) of 2-ethyl-4-linoleoyloxy-5-methyl-3(2H)-furanone (major) and 5-ethyl-4-linoleoyloxy-2-methyl-3(2H)-furanone (minor) was obtained.

(a) Characteristic properties: Yellow clear oil (b) IR spectrum $v_{max}$ (cm$^{-1}$, film): 2980, 1770, 1720, 1640 and 1190 (c) $^1$H-NMR spectrum δ (ppm in CDCl$_3$): 0.89 (t, J=6.71 Hz, 3H), 1.01 (t, J=7.0 Hz, 3H) (major), 1.13–2.03 (m, 22H), 1.13–2.03 (m, 4H) (minor), 2.17 (s, 3H) (major), 2.30–2.70 (m, 2H) (minor), 2.50 (q=J=7.5 Hz, 2H) (minor), 2.53 (t, J=7.3 Hz, 2H) (major), 2.70–2.90 (m, 2H), 4.35–4.60 (m, 1H) 5.20–5.55 (m, 4H), 2.70–2.90 (m, 2H)

Preparation Example 6

Synthesis of 4-Ethoxy-2-Ethyl-5-Methyl-3(2H)-Furanone (Major) and 4-Ethoxy-5-Ethyl-2-Methyl-3 (2H)-Furanone (Minor)

Sixty per cent sodium hydride (0.85 g) was charged in a 100 ml dried three-necked flask and the atmosphere in the flask was replaced with argon. The sodium hydride was washed 3 times with pentane under an argon stream and suspended in dried tetrahydrofuran (30 ml). To the resulting suspension, a solution in dried tetrahydrofuran (3.0 ml) of 2(or 5)-ethyl-4-hydroxy-5(or 2)-methyl-3(2H)-furanone (3.0 g) was added dropwise under cooling with ice and the mixture was stirred at room temperature for 30 minutes. Subsequently, ethyl bromide (1.58 ml) was added dropwise to the resulting mixture under cooling with ice and the mixture was refluxed for 6 hours. The resulting reaction mixture solution was mixed with a 1.0N aqueous solution of HCl (10 ml) and subjected to extraction with diethyl ether (60 ml). The ether-extraction was repeated 3 times. The ether layer was washed sequentially with water and a saturated aqueous solution of sodium bicarbonate and dried over sodium sulfate. The volatile solvent was then removed under a reduced pressure and distilled off under a reduced pressure of 65–67/2.5 mmHg. Thus, a mixture (1.57 g) of 4-ethoxy-2-ethyl-5-methyl-3(2H)-furanone (major) and 4-ethoxy-5-ethyl-2-methyl-3(2H)-furanone (minor) was obtained.

(a) Characteristic properties: Colorless liquid (b) IR spectrum $v_{max}$ (cm$^{-1}$, film): 2980, 1710, 1630, 1430, 1320, 1200 and 1040 (c) $^1$H-NMR spectrum δ (ppm in CDCl$_3$): 0.97 (t, J=7.1 Hz, 3H) (major), 1.13 (t, J=7.1 Hz, 3H) (minor), 1.26 (t, J=7.1 Hz, 3H), 1.43 (d, J=7.1 Hz, 3H) (minor), 1.71–1.89 (m, 2H) (major), 2.20 (s, 3H) (major), 2.57 (q, J=7.1 Hz, 2H), 4.06 (q, J=7.1 Hz, 2H), 4.20–4.43 (m, 1H)

Experimental Example 1

Anti-Cataract Effect of 2-Ethyl-4-Hydroxy-5-Methyl-3(2H)-Furanone on Galactose Cataract (In Vitro Test)

Lenses extracted from male Crj:Wistar strain rats (7 weeks) were immersed in a TC199 bicarbonate buffer medium (10 ml) supplemented with 30 mM galactose (Nissui Pharmaceutical Co.) and cultured in the presence of 5% $CO_2$ at 37° C. for 7 days. The cultured lenses were used in the following experiments.

Five lenses were used in each group. The lenses were immersed in the same galactose-supplemented medium (10 ml) as above and 2-ethyl-4-hydroxy-5-methyl-3(2H)-furanone (TOKYO KASEI KOGYO CO., LTD., hereinafter referred to as "EHMF") was added thereto at concentrations of 0.5 mg/10 ml, 0.25 mg/10 ml and 0.1 mg/10 ml in groups 1, 2 and 3, respectively. Glutathione of a reduced type known as an active ingredient of a therapeutic agent for cataract was added to the galactose-supplemented medium containing the lenses at concentrations of 10 mg/10 ml and 5 mg/10 ml in groups 4 and 5, respectively. In control groups 6 and 7, the lenses were immersed in a galactose-supplemented medium and a galactose free medium, respectively. In all the groups, the lenses were cultured in the presence of 5% $CO_2$ at 37° C. for 7 days with daily replacements of the media.

After cultivation, the degrees of opacity in each group were scored according to the method of Hattori et al. (Nihon Ganka Gakkaishi (Acta Societatis Ophthalmologicae Japonica), Vol. 95,No. 3, pp.228–234, 1991). The lenses with no turbidity scored 0. Those with low degrees of turbidity on the cortex scored 1. Those with turbidity all over the cortex and deeper scored 3. Those with degrees in between scored 2.

The wet weights of the lenses were measured after 7 day cultivation to estimate the degrees of lens swelling. The initial wet weights of the lenses were 26–31 mg.

The average scores of lens opacity and the average wet weights of the lenses in the test groups are shown in Table 1.

TABLE 1

| Group | Medium | Test Compound | Lens Opacity Score | Lens Wet Weight (mg) |
|---|---|---|---|---|
| 1 | Galactose-Supplemented | EHMF 0.50 mg | 0** | 29.8 ± 1.0* |
| 2 | Galactose-Supplemented | EHMF 0.25 mg | 0.5 ± 0.5** | 33.6 ± 0.1* |
| 3 | Galactose-Supplemented | EHMF 0.10 mg | 1.0* | 35.0 ± 0.6 |
| 4 | Galactose-Supplemented | Glutathione 10.0 mg of Reduced Type | 1.0* | 34.2 ± 0.6* |
| 5 | Galactose-Supplemented | Glutathione 5.0 mg of Reduced Type | 2.0 | 38.8 ± 0.2 |
| 6 | Galactose-Supplemented | — | 2.3 ± 0.5 | 40.5 ± 4.4 |
| 7 | Galactose Free | — | 0** | 26.0 ± 0.7* |

*:$p < 0.05$,
**:$p < 0.01$)

The lenses cultured in the galactose free medium (group 7) maintained transparency (score 0) and did not swell. The lenses cultured in the galactose-supplemented medium (group 6) became significantly opaque (score 2.3) and swelled. The lenses cultured in the galactose-supplemented medium containing 0.5 mg/10 ml of EHMF (group 1) maintained the same degree of transparency as that of group 7 (score 0) and swelled only negligibly. The lenses cultured in the media containing 0.25 mg/10 ml and 0.1 mg/10 ml of EHMF (groups 2 and 3) exhibited higher degrees of opacity and swelling than group 1, indicating that the effect of EHMF was dose-dependent. The glutathione of a reduced type exhibited only a slight cataract inhibiting effect (score 1) in an amount of 10 mg/10 ml.

Experimental Example 2

Anti-Cataract Effect of EHMF on Spontaneous Cataract Rats (ICR/f Rats) (In Vivo Eye Instillation Test)

EHMF was dissolved in physiological saline at a concentration of 1%. To the resulting solution, dipalmitoylphosphatidylcholine (DPPC; Nihon Yushi Co.) was added at a concentration of 0.5% to form liposomes. The EHMF containing liposome solution was used as an EHMF ophthalmic solution.

In this experiment, seven male ICR/f rats (8 weeks) were used in each group. Group 1 received the EHMF ophthalmic solution. Group 2 received cataline (Senju Seiyaku Co. ). Control group 3 received physiological saline. The administration was conducted 3 times a day (morning, afternoon and evening) for 4 weeks except sundays. During the experimental period, the pupils of the rats in each group were dilated with mydrine P (SANTEN PHARMACEITI-CAL Co., LTD) every week and photographs of the lenses were taken with a camera equipped with a Medical-Nikkor™ (NIKON CORP., lens for close photographing) so as to score the degrees of lens opacity according to the method of Hattori et al. in the same manner as in Experimental Example 1 and to measure the diameter of opaque portion.

Figure 2:
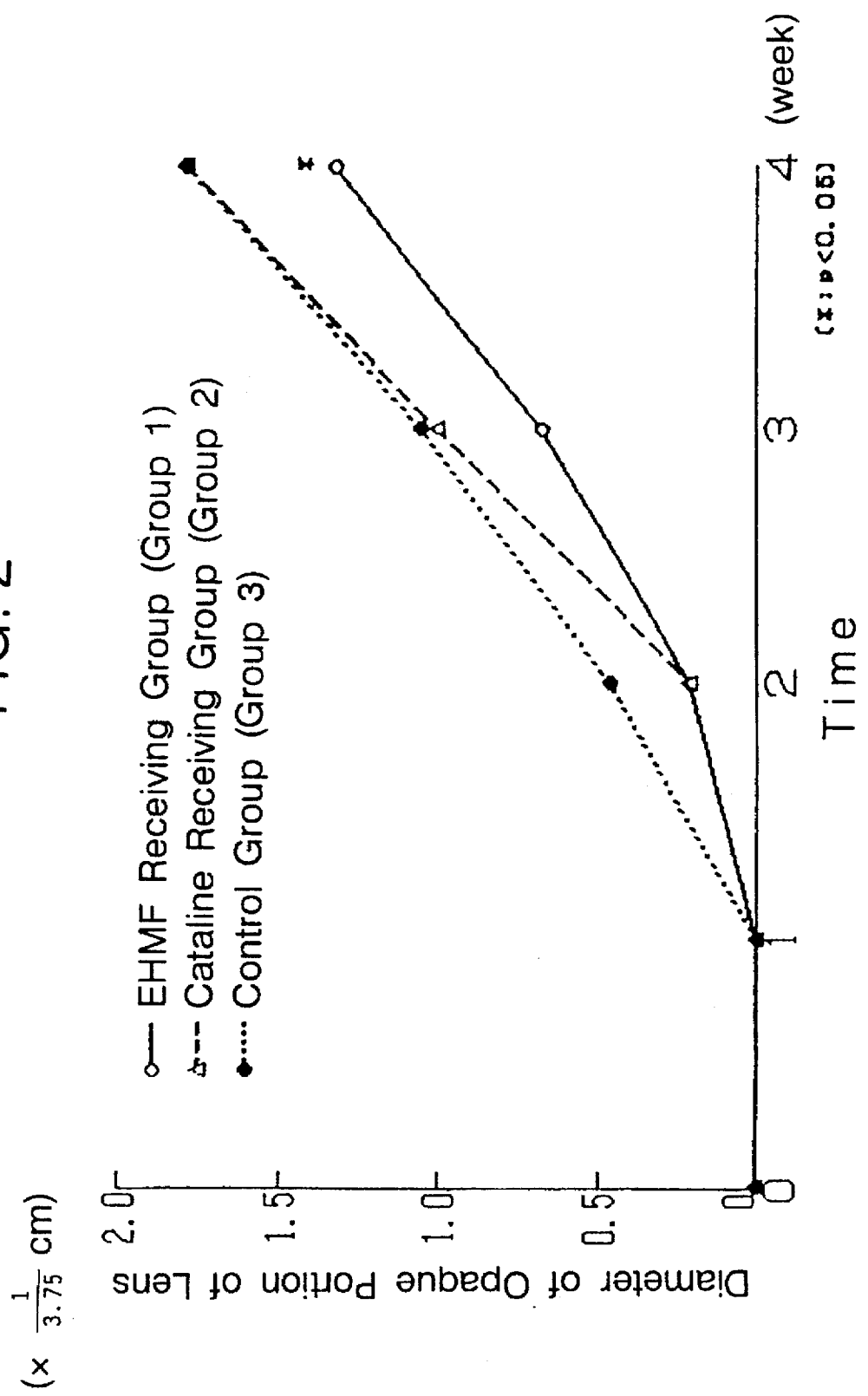
FIG. 2 shows the time-dependent changes in the average diameters of the opaque portions of the lenses in the test groups in Experimental Example 2.

The experimental results are shown in FIGS. 1 and 2. FIG. 1 shows the time-dependent changes in the average scores of lens opacity in the test groups. FIG. 2 shows the time-dependent changes in the average diameters of opaque portion of the lenses in the test groups.

In the control group having received physiological saline (group 3), significant opacity of the lenses was observed at one week after the beginning of the administration and all the rats had severe cataract at 4 weeks (FIG. 1). In the group having received EHMF (group 1), only slight opacity of the lenses was observed at one week after the beginning of the administration and the progress of cataract was significantly inhibited at 4 weeks, with the manifestation of cataract being mild (FIG. 1). The group having received cataline (group 2) showed a slight tendency to inhibit the progress of cataract at 2 weeks after the beginning of the administration; however, at 4 weeks all the rats had severe cataract as in the control group (FIG. 1).

The average diameters of opaque portions of the lenses (FIG. 2) had the same tendency as that of the lens opacity scores (FIG. 1).

Experimental Example 3

Test for the Toxicity of EHMF in a Single Administration

Five female Crj:ICR mice weighing 29–32 g (5 weeks) were used in each group. EHMF was dissolved in physiological saline at a concentration of 62.5 mg/50 ml and administered intraperitonealy to the mice in amounts of 500 mg/kg, 250 mg/kg and 100 mg/kg, respectively (groups 1–3). The mice in each group were observed for 7 days after the administration.

Neither group of mice had cases of death. At day 7 of the administration, each group was subjected to postmortem examination and the histopathological examination of various organs, showing no evidence for abnormalities. These facts revealed that EHMF had a very low toxicity level.

Experimental Example 4

Anti-Cataract Effect of 2,5-Dimethyl-4-Pivaloyloxy-3(2H)-Furanone on Galactose Cataract
(In Vitro Test)

Lenses extracted from male Crj:Wistar strain rats (7 weeks) were immersed in a TC199 bicarbonate buffer medium (10 ml) supplemented with 30 mM galactose (Nissui Pharmaceutical Co.) and cultured in the presence of 5% $CO_2$ at 37° C. for 7 days. The cultured lenses were used in the following experiments.

Five lenses were used in each group. The lenses were immersed in the same galactose-supplemented medium (10 ml) as above and the 2,5-dimethyl-4-pivaloyloxy-3(2H)-furanone (hereinafter referred to as "HDMF trimethylacetic acid monoester") prepared in Preparation Example 1 was added thereto at concentrations of 0.5 mg/10 ml, 0.1 mg/10 ml and 0.01 mg/10 ml in groups 1, 2 and 3, respectively. Glutathione of a reduced type known as an active ingredient of a therapeutic agent for cataract was added to the galactose-supplemented medium containing the lenses at concentrations of 10 mg/10 ml and 5 mg/10 ml in groups 4 and 5, respectively. In control groups 6 and 7, the lenses were immersed in a galactose-supplemented medium and a galactose free medium, respectively. In all the groups, the lenses were cultured in the presence of 5% $CO_2$ at 37° C. for 7 days with daily replacements of the media.

After cultivation, the degrees of opacity in each group were scored by the same method as in Experimental Example 1. In addition, the wet weights of the lenses were measured after 7 day cultivation to estimate the degrees of lens swelling.

The average scores of lens opacity and the average wet weights of the lenses in the test groups are shown in Table 2.

TABLE 2

| Group | Medium | Test Compound | Lens Opacity Score | Lens Wet Weight (mg) |
|---|---|---|---|---|
| 1 | Galactose-Supplemented | HDMF 0.50 mg Trimethylacetic Acid Monoester | 0** | 35.0* |
| 2 | Galactose-Supplemented | HDMF 0.10 mg Trimethylacetic Acid Monoester | 0.3 ± 0.5** | 36.5 ± 0.3* |
| 3 | Galactose-Supplemented | HDMF 0.01 mg Trimethylacetic Acid Monoester | 1.6 ± 0.5* | 41.0 ± 0.7** |
| 4 | Galactose-Supplemented | Glutathione 10.0 mg of Reduced Type | 1.0* | 37.0 ± 0.6** |
| 5 | Galactose-Supplemented | Glutathione 5.0 mg of Reduced Type | 2.0 | 42.0 ± 0.8 |
| 6 | Galactose-Supplemented | — | 2.6 ± 0.5 | 46.5 ± 1.6 |
| 7 | Galactose Free | — | 0** | 31.0 ± 0.6** |

*:$p < 0.05$,
**:$p < 0.01$

The lenses cultured in the galactose free medium (group 7) maintained transparency (score 0) and did not swell. The lenses cultured in the galactose-supplemented medium (group 6) became significantly opaque (score 2.6) and swelled. The lenses cultured in the galactose-supplemented medium containing 0.5 mg/10 ml of HDMF trimethylacetic acid monoester maintained the same degree of transparency as that of group 7 (score 0) and swelled only negligibly. The lenses cultured in the media containing 0.10 mg/10 ml and 0.01 mg/10 ml of HDMF trimethylacetic acid monoester (groups 2 and 3) exhibited higher degrees of opacity and swelling than group 1, indicating that the effect of HDMF trimethylacetic acid monoester was dose-dependent. The glutathione of a reduced type exhibited only a slight cataract inhibiting effect (score 1) in an amount of 10 mg/10 ml.

Experimental Example 5

Anti-Cataract Effect of HDMF Trimethylacetic Acid Monoester on Spontaneous Cataract Rats
(ICR/f Rats) (In Vivo Eye Instillation Test)

HDMF trimethylacetic acid monoester was dissolved in physiological saline at a concentration of 1%. To the resulting solution, dipalmitoylphosphatidylcholine (DPPC; Nihon Yushi Co.) was added at a concentration of 0–5% to form liposomes. The HDMF trimethylacetic acid monoester containing liposome solution was used as a HDMF trimethylacetic acid monoester ophthalmic solution.

In this experiment, seven male ICR/f rats (8 weeks) were used in each group. Group 1 received the HDMF trimethylacetic acid monoester ophthalmic solution. Group 2 received cataline (Senju Seiyaku Co.). Control group 3 received physiological saline. The administration was conducted 3 times a day (morning, afternoon and evening) for 4 weeks except sundays. During the experimental period, the pupils of the rats in each group were dilated with mydrine P (SANTEN PHARMACEITICAL Co., LTD.) every week and photographs of slit images of the rat lenses and whole images of anterior portions of the rat eyes were taken with a Nikon zoom slit lamp microscope FS-3 (NIKON CORP.); the images were classified for cataract in six stages of 0–5 according to the method of Nishida et al. (ATARASHIIGANKA (journal of the Eye), vol. 2, No. 9, pp.1307–1312, 1985). The ICR/f rats used in this experiment had already reached stage 3 (no lens opacity was observed with the naked eye but slight turbidity was recognized in the slit image of posterior subcapsular cortex) at the start of the experiment. During the experimental period, the time when lens turbidity reached stage 4 (lens opacity was observed with the naked eye) was judged to be the onset of cataract. A cataract onset rate (%) was calculated by (the number of eyes with cataract/the total number of eyes)×100.

Figure 3:
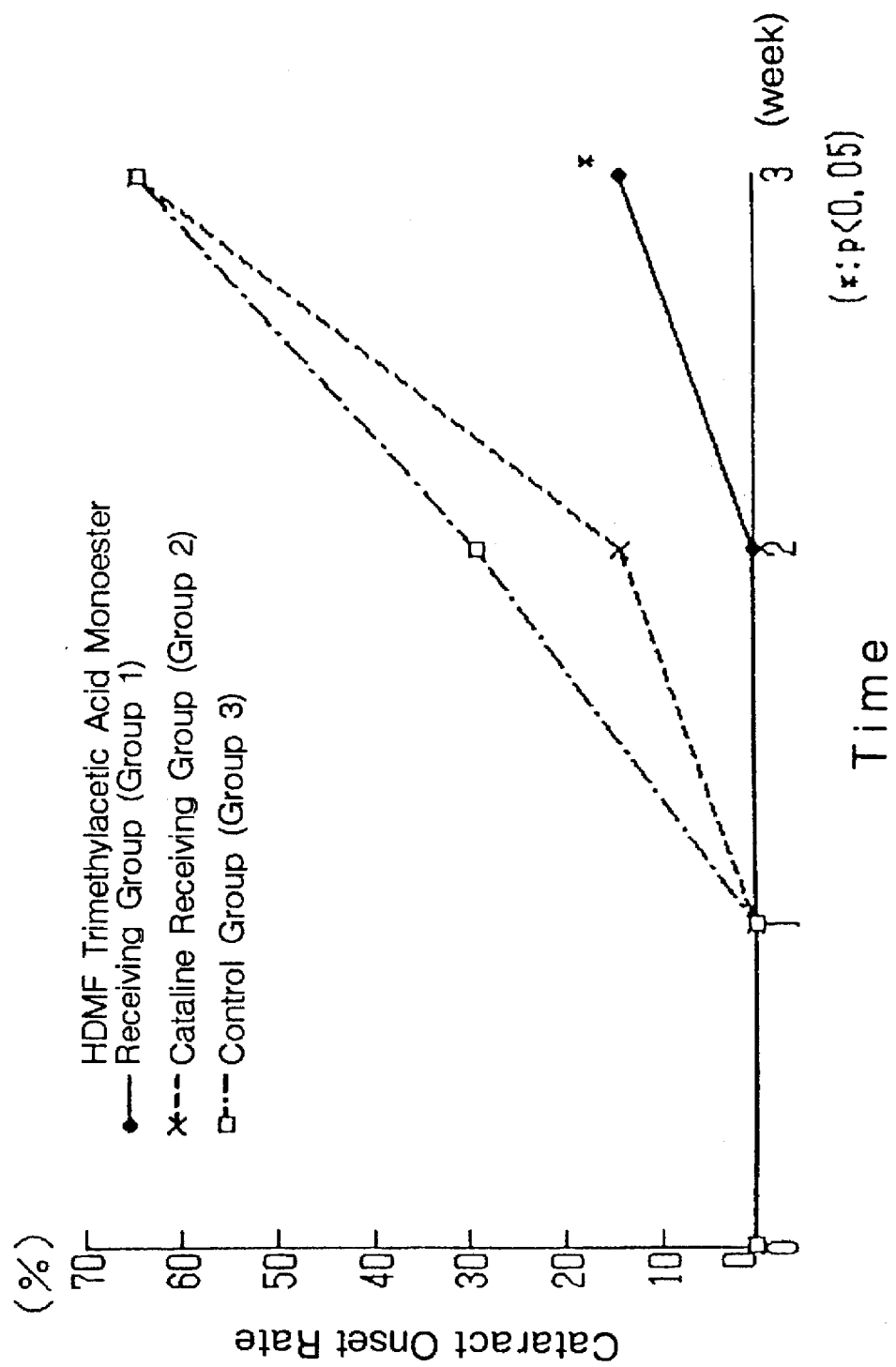
FIG. 3 shows the time-dependent changes in the cataract onset rate in the test groups in Experimental Example 5.

The time-dependent changes in the cataract onset rate (%) are shown in FIG. 3. In the control group having received physiological saline (group 3), significant opacity of the lenses was observed at one week after the beginning of the administration and the cataract onset rate was 64% at 3 weeks (FIG. 3). In the group having received HDMF trimethylacetic acid monoester (group 1), slight opacity of the lenses was observed at two weeks after the beginning of the administration and the cataract onset rate was 14% at 3 weeks (FIG. 3). The group having received cataline (group 2) showed a slight tendency to inhibit the progress of cataract at 2 weeks after the beginning of the administration and the cataract onset rate was 64% at 3 weeks as in group 3 (FIG. 3).

Experimental Example 6

Test for the Toxicity of HDMF Trimethylacetic Acid Monoester in a Single Administration Five or six male Crj:ICR mice weighing 26 g in average (5 weeks) were used in each group. HDMF trimethylacetic acid monoester was dissolved in physiological saline and administered intraperitonealy to the mice in a dose of 500 mg/kg. Physiological saline was administered to the mice in a control group in the same manner. The mice in each group were observed for 14 days.

Neither group of mice had cases of death. Neither mice exhibited any clinical symptoms and all animals showed normal increase in body weight during the experimental period. In addition, neither mice had signs of abnormal in pathological dissection after the end of the experimental period. These facts revealed that HDMF trimethylacetic acid monoester had a very low toxicity level.

Experimental Example 7

Anti-Cataract Effect of 4-Hydroxy-2, 5-Dimethyl-3 (2H)-Furanone on Galactose Cataract (In Vitro Test)

The 4-Hydroxy-2, 5-dimethyl-3(2H)-furanone (TOKYO KASEI KOGYO CO., LTD., hereinafter referred to as "HDMF") prepared in Preparation Example 2 was used rather than HDMF trimethylacetic acid monoester and examined for an in vitro anti-cataract effect by the same method as in Experimental Example 4. The results are shown in Table 3.

TABLE 3

| Group | Medium | Test Compound | Lens Opacity Score | Lens Wet Weight (mg) |
|---|---|---|---|---|
| 1 | Galactose-Supplemented | HDMF 0.50 mg | 0** | 35.1* |
| 2 | Galactose-Supplemented | HDMF 0.10 mg | 0.7 ± 0.2** | 36.9 ± 0.7** |
| 3 | Galactose-Supplemented | HDMF 0.01 mg | 2.0 ± 0.5* | 42.5 ± 2.8* |
| 4 | Galactose-Supplemented | Glutathione 10.00 mg of Reduced Type | 1.0* | 37.0 ± 0.6** |
| 5 | Galactose-Supplemented | Glutathione 5.00 mg of Reduced Type | 2.0 | 42.0 ± 0.8 |
| 6 | Galactose-Supplemented | — | 2.6 ± 0.5 | 46.5 ± 1.6 |
| 7 | Galactose Free | — | 0** | 31.0 ± 0.6** |

*:$p < 0.05$,
**:$p < 0.01$)

Table 3 shows that HDMF had as remarkable an anti-cataract effect as the HDMF trimethylacetic acid monoester used in Experimental Example 4.

Experimental Example 8

Anti-Cataract Effect of HDMF on Spontaneous Cataract Rats (ICR/f Rats) (In Vivo Test)

HDMF was used rather than HDMF trimethylacetic acid monoester and examined for an anti-cataract effect through eye instillation by the same method as in Experimental Example 5. The results are shown in FIG. 4.

FIG. 4 shows that HDMF exhibited as remarkable an anti-cataract effect through eye instillation as the HDMF trimethylacetic acid monoester used in Experimental Example 5.

Experimental Example 9

Anti-Cataract Effect of HDMF on Spontaneous Cataract Rats (ICR/f Rats) (In Vivo Oral Administration Test)

Seven or eight male ICR/f rats weighing 190 g in average (8 weeks) were used in each group. The rats in group 1 were allowed MF powder feeds (Oriental Yeast Co., Ltd.) containing 0.1% HDMF ad libitum for 3 weeks. The rats in control group 2 were allowed MF powder feeds ad libitum for 3 weeks. During the experimental period, photographs were taken every week and the cataract onset rates was calculated by the same method as in Experimental Example 5. The results are shown in FIG. 5. In the control group (group 2), significant opacity of the lenses was observed at one week after the beginning of the administration and the cataract onset rate was 64% at 3 weeks (FIG. 5). In the group having received the 0.1% HDMF containing feeds (group 1), no opacity of the lenses was observed during the experimental period and the cataract onset rate was 0% at 3 weeks (FIG. 5). The HDMF intake of the rats in the group having received the 0.1% HDMF containing feeds was 77 mg/kg/day in average.

Experimental Example 10

Test for the Toxicity of HDMF in a Single Administration

Five female Crj:ICR mice weighing 29–32 g (5 weeks) were used in each group. HDMF was dissolved in physiological saline at a concentration of 62.5 mg/50 ml and administered intraperitonealy to the mice in amounts of 500 mg/kg, 250 mg/kg and 100 mg/kg, respectively (groups 1–3). The mice in each group were observed for 7 days after the administration.

Neither group of mice had cases of death. At day 7 of the administration, each group was subjected to postmortem examination and the histopathological examination of various organs, showing no evidence for abnormalities. These facts revealed that HDMF had a very low toxicity level.

Experimental Example 11

Anti-Cataract Effect of Various Furanone Derivatives (In Vivo Eye Instillation Test)

The furanone derivatives synthesized in Preparation Examples 1–6 were examined for an anti-cataract effect on spontaneous cataract rats (ICR/f rats) by the same vivo eye instillation test as in Experimental Example 5.

Table 4 shows the number of eyes with cataract divided by the total number of eyes at 3 weeks after the beginning of the administration of the various furanone derivative containing ophthalmic solutions. Physiological saline was administered to a control group.

TABLE 4

| Furanone Derivative | Anti-cataract Effect at 3 Weeks The Number of Eyes with Cataract/The Total Number of Eyes |
|---|---|
| Control | 10/18 |
| 1 (Synthesised in Preparation Example 1) | 2/14 |
| 2 (Synthesised in Preparation Example 2) | 5/14 |
| 3 (Synthesised in Preparation Example 3) | 5/14 |
| 4 (Synthesised in Preparation Example 4) | 5/12 |
| 5 (Synthesised in Preparation Example 5) | 7/14 |
| 6 (Synthesised in Preparation Example 6) | 5/12 |

1 :2,5-Dimethyl-4-pivaloyloxy-3(2H)-furanone
2 :2-Ethyl-5-methyl-4-pivaloyloxy-3(2H)-furanone (Major ingredient)
3 :4-Acetoxy-2-ethyl-5-methyl-3(2H)-furanone (Major ingredient)
4 :4-Butyryloxy-2-ethyl-5-methyl-3(2H)-furanone (Major ingredient)
5 :2-Ethyl-4-linoleoyloxy-5-methyl-3(2H)-furanone (Major ingredient)
6 :4-Ethoxy-2-ethyl-5-methyl-3(2H)-furanone (Major ingredient)

Table 4 shows that all the 3(2H)-furanone derivatives tested had a potent anti-cataract effect.

Hence, it was confirmed that the 3(2H)-furanone derivatives of the present invention are very useful as agents for preventing and/or treating cataract.

Formulation Example 1

Ophthalmic Solution

The following ingredients were dissolved in sterile purified water to a total volume of 100 ml. The solution was adjusted to pH 6.0 with sodium hydroxide.

| HDMF trimethylacetic acid monoester | 1.0 g |
|---|---|
| Boric acid | 0.7 g |
| Sodium chloride | 0.6 g |
| Methyl p-oxybenzoate | 0.02 g |
| Chlorobutanol | 0.3 g |

Formulation Example 2

Oral Medicine

The following ingredients were used to make a tablet.

| HDMF trimethylacetic acid monoester | 100 mg |
|---|---|
| Lactose | 80 mg |
| Starch | 17 mg |
| Magnesium stearate | 3 mg |

Formulation Example 3

Injection Solution

The following ingredients were mixed and the mixture was filtered aseptically through a MINI CAPSULE filter of 0.45 μm (Gelman Science Co.). The filtrate was charged in 2-ml portions into glass ampules and sealed by heating to make injection solutions.

| HDMF trimethylacetic acid monoester | 1.5 g |
|---|---|
| Sodium Chloride | 0.6 g |
| Distilled Water for Injection Solution | 100 ml |

Formulation Example 4

Ophthalmic Solution

The following ingredients were dissolved in sterile purified water to a total volume of 100 ml. The solution was adjusted to pH 6.0 with sodium hydroxide.

| HDMF | 1.0 g |
|---|---|
| Boric acid | 0.7 g |
| Sodium chloride | 0.6 g |
| Methyl p-oxybenzoate | 0.02 g |
| Chlorobutanol | 0.3 g |

Formulation Example 5

Oral Medicine

The following ingredients were used to make a tablet.

| HDMF | 100 mg |
|---|---|
| Lactose | 80 mg |
| Starch | 17 mg |
| Magnesium stearate | 3 mg |

Formulation Example 6

Injection Solution

The following ingredients were mixed and the mixture was filtered aseptically through a MINI CAPSULE filter of 0.45 μm (Gelman Science Co.). The filtrate was charged in 2-ml portions into glass ampules and sealed by heating to make injection solutions.

| HDMF | 1.5 g |
|---|---|
| Sodium Chloride | 0.6 g |
| Distilled Water for Injection Solution | 100 ml |

Formulation Example 7

Ophthalmic Solution

The following ingredients were dissolved in sterile purified water to a total volume of 100 ml. The solution was adjusted to pH 6.0 with sodium hydroxide.

| EHMF | 1.0 g |
|---|---|
| Boric acid | 0.7 g |
| Sodium chloride | 0.6 g |
| Methyl p-oxybenzoate | 0.02 g |
| Chlorobutanol | 0.3 g |

Formulation Example 8

Oral Medicine

The following ingredients were used to make a tablet.

| EHMF | 100 mg |
|---|---|
| Lactose | 80 mg |
| Starch | 17 mg |
| Magnesium stearate | 3 mg |

Formulation Example 9

Injection Solution

The following ingredients were mixed and the mixture was filtered aseptically through a MINI CAPSULE filter of 0.45 μm (Gelman Science Co.). The filtrate was charged in 2-ml portions into glass ampules and sealed by heating to make injection solutions.

| | |
|---|---|
| EHMF | 1.5 g |
| Sodium Chloride | 0.6 g |
| Distilled Water for Injection Solution | 100 ml |

Preparation Example 7

Synthesis of Ethyl 3-(4-Hydroxy-5-Oxo-3-Phenyl-2-Hydro-2-Furyl)Propionate

Methyl phenylpyruvate (4.34 g) and ethyl 3-formylpropionate (6.3 g) were dissolved in N,N-dimethylformamide (92 ml). To the resulting solution, 1,8-diazabicyclo[5,4,0]undecene (4.1 ml) was added dropwise under stirring. The mixture was stirred at 0° C. for 2 hours and the solvent was then removed under a reduced pressure. Subsequently, the residue was mixed with 1N diluted hydrochloric acid (20 ml) and subjected to extraction with ethyl acetate (60 ml). The extraction was repeated 3 times. The organic layer was washed sequentially with diluted hydrochloric acid, water and a saturated saline solution and dried over sodium sulfate. The organic layer was then concentrated and applied to a silica gel column for separation and purification. Thus, ethyl 3-(4-hydroxy-5-oxo-3-phenyl-2-hydro-2-furyl)propionate (3.60 g) was obtained (yield: 53.5%).

(a) IR spectrum $v_{max}$ (cm$^{-1}$, film): 1750, 1710, 1460, 1460(s), 1380, 1270 and 1150 (b) $^1$H-NMR spectrum δ (ppm in CDCl$_3$, 60 MHz): 1.27 (t, J=7.1 Hz, 3H), 1.68–1.87 (m, 1H), 2.39–2.68 (m, 3H), 4.16 (q, J=7.1 Hz, 2H), 5.51 (dd, J$_1$=1.6 Hz, J$_2$=8.9 Hz), 7.36–7.79 (m, 5H)

Comparative Example 1

Anti-Cataract Effect of Ethyl 3-(4-Hydroxy-5-Oxo-3-Phenyl-2-Hydro-2-Furyl)Propionate on Galactose Cataract (In Vitro Test)

A 2(5H)-furanone derivative known as a therapeutic agent for cataract was examined for an anti-cataract effect on galactose cataract.

The ethyl 3-(4-hydroxy-5-oxo-3-phenyl-2-hydro-2-furyl) propionate prepared in Preparation Example 7 was used rather than HDMF trimethylacetic acid monoester and examined for an anti-cataract effect by the same method as in Experimental Example 4. The results are shown in Table 5.

TABLE 5

| Group | Medium | Test Compound | Lens Opacity Score | Lens Wet Weight (mg) |
|---|---|---|---|---|
| 1 | Galactose-Supplemented | 2(5H)-Furanone 0.50 mg Derivative | 2.0 ± 0.8* | 40.7 ± 4.5 |
| 2 | Galactose-Supplemented | 2(5H)-Furanone 0.10 mg Derivative | 2.3 ± 1.3 | 43.7 ± 2.9 |
| 3 | Galactose-Supplemented | 2(5H)-Furanone 0.01 mg Derivative | 2.5 ± 0.9 | 45.3 ± 2.1 |

*:p < 0.05, 2(5H)-Furanone:ethyl 3-(4-hydroxy-5-oxo-3-phenyl-2-hydro-2-furyl)propionate)

The results of Experimental Examples 4 and Comparative Example 1 showed that the anti-cataract effect of the 3(2H)-furanone derivative was more effective than that of the 2(5H)-furanone derivative by a factor of about 7 at a level of 0.10 mg.

Preparation Example 8

Synthesis of 3-(4-Hydroxy-5-Oxo-3-Phenyl-2-Hydro-2-Furyl)Propionic Acid

The ethyl 3-(4-hydroxy-5-oxo-3-phenyl-2-hydro-2-furyl) propionate (2.0 g) prepared in Preparation Example 7 was dissolved in a mixture solution (64 ml) of tetrahydrofuran and methanol (2:1 (v/v)). To the resulting solution, a 1N aqueous solution (21 ml) of sodium hydroxide was added dropwise at 0° C. under stirring and the mixture was stirred at room temperature for 20 hours. The resulting reaction mixture was concentrated under a reduced pressure, mixed with 1N diluted hydrochloric acid (20 ml) and subjected to extraction with ethyl acetate (40 ml). The extraction was repeated 3 times. The organic layer was washed with a saturated saline solution and dried over sodium sulfate. The organic layer was then concentrated and applied to a silica gel column for separation and purification. Thus, 3-(4-hydroxy-5-oxo-3-phenyl-2-hydro-2-furyl)propionic acid (0.81 g) was obtained (yield: 45.2%).

(a) IR spectrum $v_{max}$ (cm$^{-1}$, film): 3170, 1750(s), 1700, 1460(s), 1380, 1320, 1250, 1210 and 1170 (b) $^1$H-NMR spectrum δ (ppm in CDCl$_3$, 60 MHz): 1.63–1.80 (m, 1H), 2.34–2.56 (m, 3H), 5.51 (dd, J$_1$=2.1 Hz, J$_2$=8.4 Hz), 7.40–7.80 (m, 5H)

Comparative Example 2

Anti-Cataract Effect of 3-(4-Hydroxy-5-Oxo-3-Phenyl-2-Hydro-2-Furyl)Propionic Acid on Spontaneous Cataract Rats (ICR/f Rats) (In Vivo Eye Instillation Test)

A 2(5H)-furanone derivative known as a therapeutic agent for cataract was examined for an anti-cataract effect on galactose cataract.

The 3-(4-hydroxy-5-oxo-3-phenyl-2-hydro-2-furyl) propionic acid prepared in Preparation Example 8 was used rather than HDMF trimethylacetic acid monoester and examined for an anti-cataract effect by the same method as in Experimental Example 5. The results are shown in FIG. 6.

The results of Experimental Examples 5 and Comparative Example 2 showed that the anti-cataract effect of the 3(2H)-furanone derivative was more effective than that of the 2(5H)-furanone derivative by a factor of about 3.5 at 3 weeks.

We claim:

1. A method for prevention and/or treatment of cataract which comprises using a furanone derivative having a 3(2H)-furanone skeleton as a mother skeleton or its pharmaceutically acceptable salt with effective dosage.

2. A method according to claim 1, wherein said furanone derivative is shown in formula(1):

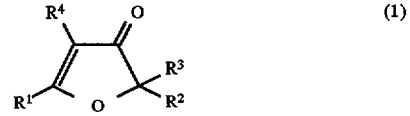

wherein R$^1$, R$^2$, R$^3$, and R$^4$ are identical or different, independently, and are groups selected from the group consisting of a hydrogen atom, halogen atom, hydroxy group, amino group, mercapto group, carboxy group, carbamoyl group, alkyl group, alkenyl group, alkynyl group, alkoxy group, alkenyloxy group, alkynyloxy group, aryloxy group, aryl group, aralkyl group, arylalkoxy group, acyloxy group, and alkoxycarbonyl group.

3. A method according to claim 2, wherein $R_1$, $R_2$, $R_3$, and $R_4$ are groups selected from the group consisting of a hydrogen atom, hydroxy group, alkyl group, alkoxy group, and acyloxy group.

4. A method according to claim 1, wherein said furanone derivative is shown in formula(2):

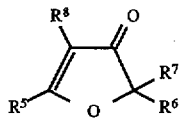
(2)

wherein $R_5$, $R_6$, and $R_7$ are identical or different, independently, and are a hydrogen atom or alkyl group, and $R_8$ is an alkoxy group.

5. A method according to claim 1, wherein said furanone derivative is a 4-acyloxy-3(2H)-furanone derivative shown in formula(3):

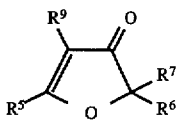
(3)

wherein $R_5$, $R_6$, and $R_7$ are identical or different, independently, and are a hydrogen atom or alkyl group, and at least one of $R_6$ and $R_7$ is a hydrogen atom; and wherein R9 is an acyloxy group comprising a hydrocarbon moiety selected from the group consisting of a saturated and unsaturated aliphatic hydrocarbon group having 2 to 22 carbon atoms and an aryl group.

6. A method according to claim 1, wherein said furanone derivative is at least one derivative selected from the group consisting of 2, 5-dimethyl-4-pivaloyloxy-3 (2H)-furanone, 2-ethyl-5-methyl-4-pivaloyloxy-3(2H )-furanone, 5-ethy-2-methyl-4-pivaloyloxy-3(2H )-furanone, and 4-hydroxy-2, 5-dimethyl-3(2H)-furanone.

7. A method according to one of claims 1 to 6, wherein said pharmaceutically acceptable salt of said furanone derivative is a member selected from the group consisting of alkaline metal salt, alkaline earth metal salt, ammonium salt, and amine salt.

8. A composition comprising a 4-alkoxy-3(2H)-furanone derivative shown in formula(2):

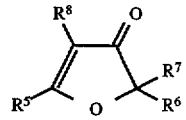
(2)

wherein $R_5$, $R_6$ and $R_7$ are identical or different, independently, and are a hydrogen group or alkyl group, and $R_8$ is an alkoxy group.

9. A composition comprising a 4-acyloxy-3(2H)-furanone derivative shown in formula(3):

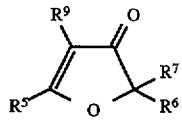
(3)

wherein $R_5$, $R_6$, and $R_7$ are identical or different, independently, and are a hydrogen atom or alkyl group, and at least one of $R_6$ and $R_7$ is a hydrogen atom; and wherein $R_9$ is an acyloxy group comprising a hydrocarbon moiety selected from the group consisting of a saturated and unsaturated aliphatic hydrocarbon group having 2 to 22 carbon atoms and an aryl group.

* * * * *